US008962558B2

(12) United States Patent
Van Groeninghen

(10) Patent No.: US 8,962,558 B2
(45) Date of Patent: Feb. 24, 2015

(54) METHODS FOR REDUCING GNRH-POSITIVE TUMOR CELL PROLIFERATION USING THE GNRH ANTAGONIST IN3

(76) Inventor: Johannes C. Van Groeninghen, Dortmund (DE)

( * ) Notice: Subject to any disclaimer, the term of this patent is extended or adjusted under 35 U.S.C. 154(b) by 0 days.

(21) Appl. No.: 13/430,999

(22) Filed: Mar. 27, 2012

(65) Prior Publication Data

US 2012/0238494 A1 Sep. 20, 2012

Related U.S. Application Data

(63) Continuation-in-part of application No. 12/701,284, filed on Feb. 5, 2010, now abandoned, which is a continuation-in-part of application No. 10/327,621, filed on Dec. 20, 2002, now Pat. No. 7,695,722, which is a continuation-in-part of application No. 09/446,996, filed as application No. PCT/DE98/01902 on Jul. 3, 1998, now abandoned.

(30) Foreign Application Priority Data

Jul. 4, 1997 (DE) .................................. 197 28 737

(51) Int. Cl.
| | |
|---|---|
| *A61K 38/09* | (2006.01) |
| *G01N 33/53* | (2006.01) |
| *A61K 38/24* | (2006.01) |
| *A61K 31/00* | (2006.01) |
| *A61K 31/519* | (2006.01) |
| *A61K 31/704* | (2006.01) |
| *A61K 38/18* | (2006.01) |
| *A61K 45/06* | (2006.01) |
| *G01N 33/574* | (2006.01) |
| *G01N 33/76* | (2006.01) |
| *A61K 38/17* | (2006.01) |

(52) U.S. Cl.
CPC .............. *A61K 31/00* (2013.01); *A61K 31/519* (2013.01); *A61K 31/704* (2013.01); *A61K 38/09* (2013.01); *A61K 38/1816* (2013.01); *A61K 45/06* (2013.01); *G01N 33/57492* (2013.01); *G01N 33/76* (2013.01); *A61K 38/1709* (2013.01); *G01N 2333/726* (2013.01)
USPC ....... 514/10.3; 424/198.1; 435/7.1; 435/69.4; 530/313; 530/398; 514/10.4; 514/10.6

(58) Field of Classification Search
None
See application file for complete search history.

(56) References Cited

U.S. PATENT DOCUMENTS

| | | | |
|---|---|---|---|
| 5,760,000 A | 6/1998 | Habibi | |
| 5,985,834 A | 11/1999 | Engel | |
| 6,140,066 A | 10/2000 | Lorberboum-Galski et al. | |
| 6,242,421 B1 | 6/2001 | Bowen | |
| 6,933,271 B2 | 8/2005 | Yarkoni et al. | |
| 7,344,699 B2 | 3/2008 | Lappin et al. | |
| 7,695,917 B2 * | 4/2010 | Conn .............................. 435/7.1 |
| 2009/0170759 A1 | 7/2009 | Smith-Swintosky et al. | |

FOREIGN PATENT DOCUMENTS

| | | | | |
|---|---|---|---|---|
| CA | 2295577 | * | 1/1999 | ............. G01N 33/53 |
| WO | WO 90/09799 | | 9/1990 | |

OTHER PUBLICATIONS van Muijen et al., Establishment and characterization of a human melanoma cell line (MV3) which is highly metastatic in nude mice, Int. J. of Cancer, 48, 85-91, 1991.*
Schadendorf et al. Metastatic potential of human melanoma cells in nude mice—characterization of phenotype, cytokine secretion and tumor-associated antigens, Br. J. Cancer, 74, 194-199, 1996.*
Nagy et al.,, Cytotoxic analogs of luteinizing hormone-releasing hormone containing doxorubicin or 2-pyrrolinodoxorubicin, a derivative 500-1000 times more potent. Proc. Natl. Acad. Sci. USA, 93, 7269-7273, 1996.*
Finch et al. Plasma membrane expression of gonadotropin-releasing hormone receptors: regulation by peptide and nonpeptide antagonists, Mol. Endo. 24, 423-435, 2010—Online Pub Dec. 15, 2009.*
Marrelli et al. Novel insights into GnRH receptor activity: Role in the control of human glioblastoma cell proliferation, Oncology reports, 21, 1277-1282, 2009.*
Yang et al., Cytotoxic Activity of Gonadotropin-Releasing Hormone (GnRH)—Pokeweed Antiviral Protein Conjugates in Cell Lines Expressing GnRH Receptors, Endocrinolgy, 144, 1456-1463, 2003.*
Limonta et al., The biology of GnRH: Role in control of tumor growth and progression in humans. Frontiers in Neuroendocrinology, 24, 279-295, 2003.*
Declaration of Loberboum-Glaski dated Jun. 11, 2003 in support of U.S. Appl. No. 09/147,346, issued as UIS. Patent No. 6,933,271 B2.
Keller et al. Human Malig Melanomas Express Receptors for LHRH Allowing Targeted Therapy w/Cytotoxic LH Analogue, Cancer Research, Jul. 1, 2005, pp. 5857-5863, vol. 65, No. 13.
Norwood Immunology, Phase II Clinical Trial, Melanoma Cancer Vaccine (Nov. 17, 2005) <http://biz.yahoo.com/bw/051117/20051117005541.html?.v=1>.

(Continued)

*Primary Examiner* — Elly-Gerald Stoica
(74) *Attorney, Agent, or Firm* — Grund Intellectual Property Group; Stacey J. Farmer

(57) ABSTRACT

A method for recognizing and evaluating the presence and function of GnRH receptors on tumor cells including those originating in the brain and/or nervous system and/or the meninges and/or reactive neuroglia cells and/or primitive neuroectodermal tumor cells and/or on Kaposi sarcoma is provided. Furthermore, a method for reducing degenerate GnRH-positive tumor cells and/or for decreasing cellular replication of the above GnRH-positive tumor cells comprising administering to a cell or to a subject a replication decreasing amount of a GnRH agonist and/or GnRH antagonist and/or an erythropoietin agonist, and/or a thrombopoietin agonist, and/or a endothelin antagonist and/or a gonadotropin inhibiting hormone agonist is also provided. Furthermore, a diagnostic kit for detecting GnRH receptors on tumor cells according to the present methods is disclosed.

19 Claims, 20 Drawing Sheets

(56) References Cited

OTHER PUBLICATIONS

MDACC Study Summary No. 2004-0502 (Jan. 9, 2006) <http://utm-ext01a.mdacc.tmc.edu/dept/prot/clinicaltrialswp.nsf/Index/2004-0502>.
Van Groeninghen et al. Effects of luteinising-hormone-releasing hormone on nervous-system tumours, The Lancet, Aug. 1, 1998, pp. 372-373, vol. 352, No. 9125.
Moretti et al. Locally exprssed LHRH Receptors Mediate Oncostatic & Antimetastatic Activity of LHRH Agonists on Melanoma Cells J. Clin. Endocrinol. Metab. 2002 87(8):3791-7.
Moretti et al. Inhibitory activity of luteinizing hormone-releasing hormone on tumor growth and progression, Endocrine-Releated Cancer (2003) 10(2):161-7.
Limoneta et al. The biology of GnRH: Role in the control of tumor growth and progression in humans, Front. Neuroendocrinol. 2003, 24:279-295.
Alexander et al. GnRH mRNA Expression by Human Pituitary Tumors in vitro, J. Clin. Invest. 93: 2332-2339, Jun. 1994.
Karande et al. Establishment of immunological probes to study human GnRH receptors, ScienceDirect-Molecular & Cell. Endocrinology (Abstract) (Nov. 16, 1999).
Abstract No. XP-002090711 (Biological Abstracts, Abstract No. PREV1994973660906 (1994).
Abstract No. XP-002090712 (Chemical Abstracts, vol. 124, No. 23 (1996).
Ackerman et al. Cancer Lett. 81(2):177-184 (1994) (Abstract only).
Badr et al. Synapse 1(6): 567-571 (1987) (Abstract Only).
Karande et al. Mol. Cell. Endocrinol. 114(1-2) 51-56 (1995) (Abstract Only).
Leung et al. Biol. Signals, 5:63-69 (1996).
Compagne et al. British J. Cancer 2000, vol. 83, pp. 1-5.
Johnson et al. Brit. J. Cancer 2001, vol. 84, pp. 1424-1431.
Shi et al. J. Chem. Inf. Comput. Sci. 2000, vol. 40, pp. 367-379.
Rote Liste, 1997 (Arzneimittelverzeichnis für Deutschland), Pharmaceutical Listing for Germany.
Farrell et al. The Erythropoietin Receptor and Its Expression in Tumor Cells and Other Tissues, The Oncologist 2004; 9 (Suppl 5):18-30.

\* cited by examiner

METHODS FOR REDUCING GNRH-POSITIVE TUMOR CELL PROLIFERATION USING THE GNRH ANTAGONIST IN3

CROSS-REFERENCE TO RELATED APPLICATION

This application is a continuation in part of co-pending U.S. application Ser. No. 12/701,284, filed on Feb. 5, 2010, which is a continuation in part of U.S. application Ser. No. 10/327,621, filed on Dec. 20, 2002, now U.S. Pat. No. 7,695, 722, issued on Apr. 13, 2010, which is a continuation in part of U.S. application Ser. No. 09/446,996, filed on Dec. 30, 1999, now abandoned, the contents of all are incorporated by reference; the latter application was a national phase entry under 35 U.S.C. §371 of International Patent Application PCT/DE98/01902, filed Jul. 3, 1998, published as International Patent Publication WO 99/01764 on Jan. 14, 1999.

FIELD OF THE INVENTION

The present invention relates to tumor diagnosis and therapy. In particular, it is directed to the therapy of tumors bearing GnRH receptors using GnRH agonists, GnRH antagonists, and/or a combination thereof.

BACKGROUND OF THE INVENTION

Post-operative treatment of prostate and mammary carcinomas using gonadotropin releasing hormone (or "GnRH", also referred to as luteinizing hormone releasing hormone, or "LHRH" in the literature) agonists is a standard treatment; cf. Gonzalez-Barcena et al., 1994, The Prostate 24, 84-92; Emons and Schally, 1994, Human Reproduction Update 9, No. 7, 1364-1379. The GnRH receptor is a well-known target in tumor therapy.

The amino acid sequence of human GnRH has been characterized as pGlu-His-Trp-Ser-Tyr-Gly-Leu-Arg-Pro-Gly-NH$_2$. A second form, or isoform of GnRH, referred to as "GnRH-II", is widely conserved among vertebrates, including humans, and has been shown to exhibit a high binding affinity for the GnRH receptor both in primate and human (Davidson, J. S., McArdle, C. A., Davies, P. et al. (1996) Asn$^{109}$ of the gonadotropin-releasing hormone receptor is a critical determinant of potency for agonists containing C-terminal glycamide. *J. Biol. Chem.*, 271, 15510-15514; Sherwood, N. M., Lovejoy, D. A. and Coe, I. R. (1993) Origin of mammalian gonadotropin-releasing hormones. *Endocr. Rev.*, 14, 241-254. C-terminal glycamide. *J. Biol. Chem.*, 271, 15510-15514; Lescheid, D. W., Terasawa, E., Abler, L. A. et al. (1997). Another form of GnRH that has characteristics of chicken GnRH-II is present in the primate brain *Endocrinology*, 138, 5618-5629, and has the sequence of pGlu-His-Trp-Ser-His-Gly-Trp-Tyr-Pro-Gly-NH$_2$, which differs from the mammalian GnRH sequence at the fifth, seventh and eighth amino acids (White, R. B., Eisen, J. A., Kasten, T. L. et al. (1998) Second gene for gonadotropin-releasing hormone in humans. *Proc. Natl. Acad. Sci. USA*, 95, 305-309.).

Thus, in various steroid hormone (i.e. sexual hormone) dependent malignant tumors, such as mammary carcinoma, prostate carcinoma, ovarian carcinoma, and endometrial carcinoma, a double-effect has been observed in clinical studies upon treatment with GnRH agonists, namely: 1) an indirect anti-proliferative activity through the uncoupling of the positive endocrine (estrogenous or androgenous) effect on tumor growth; and 2) a direct anti-proliferative activity by an unknown mechanism through the action of GnRH receptors on the tumor tissue itself; cf. Emons and Schally, 1994, Human Reproduction Update 9, 1364-1379.

This observed indirect effect due to steroid hormone dependence has been known for decades concerning prostate and the mammary carcinoma; cf. Gonzalez-Barcena et al., 1994, The Prostate 24, 84-92; Jonat et al., 1995, European Journal of Cancer 31A, 137-142.

The direct anti-proliferative effect of GnRH agonists and GnRH antagonists on e.g. prostate carcinomas, mammary carcinomas, and ovarian carcinomas has been confirmed by clinical studies. Several of the GnRH agonists employed in these treatments that have a direct anti-proliferative effect are known by the following trademarks of these medicaments, which are approved in Germany, for example: ZOLADEX® (goserelin acetate implant), ZOLADEX 10.8® (goserelin acetate implant), ZOLADEX GYN® (goserelin acetate implant), PROFACT®-DEPOT, PROFACT® PRO INJECTIONE/NASAL, SYNARELA®, ENANTONE MONATS-DEPOT®, UNO-ENANTONE®, ENANTONE GYN MONATS-DEPOT®, TRENANTONE®, SUPRECUR®, CARCINIL®, or DECAPEPTYL® 0.5 mg/0.1 mg, DECAPEPTYL® DEPOT, DECAPEPTYL® GYN as well as DECAPEPTYL® DIAGNOSTIK.

Research using cell cultures has revealed that GnRH receptors are present on human primary liver cell carcinomas and pancreatic adenocarcinomas. In addition, the beginning of a biochemical metabolic reaction with respect to cleavage of GnRH between tyrosine 5 and glycine 6 in rat glioma and rat neuroblastoma has been described; cf. Tao et al., 1991, Neuropeptides 20, 125-131. Ligand binding of GnRH to the GnRH receptor and its signal transduction, however, takes place in a different way, namely at the eighth amino acid of GnRH, arginine, and this exclusively occurs in the case of an intact conformation of the GnRH molecule and its amino acid side chains (Naor, Z., Schacham, Sh., Harris, D., Seger, R., and Reiss, N., 1995, Signal Transduction of the Gonadotropin Releasing Hormone (GnRH) Receptor: Cross-Talk of Calcium, Protein Kinase C (PKC), and Arachidonic Acid. Cellular and Molecular Neurobiology, vol. 15, 527-545). In a normal rat adenohypophysis, where GnRH receptors reside, GnRH leads to an increased cAMP production, however, it is still unclear whether this is a direct or an indirect effect (i.e. a paracrine interaction). For the functioning of the GnRH receptor in rat, including secretion of LH as well as an increased production of LH stimulated by GnRH, the biochemical metabolism of GnRH, e.g. by means of cAMP, plays only an indirect role (Abdilnour, G., and Bourne, G. A., 1995, Adenosine 3',5'-cyclic mono-phosphate and the self-priming effect of gonadotropin-releasing hormone. Molecular and Cellular Endocrinology, 107, 1-7). Naturally, GnRH receptors have been localized on human gonadotropin producing pituitary adenomas (Alexander, J. P., and Klibanski, A., Gonadotropin-releasing Hormone Receptor mRNA Expression by Human Pituitary Tumors In Vitro, 1994, Journal of Clinical Investigation, 93, 2332-2339).

In the case of glioma and other malignant tumors of ectodermal origin, such as malignant melanoma and, in particular in the case of diffusely growing tumors in the nervous system or in the case of metastases (formation of disseminations, for example, in other organs such as oat-cell carcinoma in the lung), life expectancy is not optimistic. The same is true for Kaposi sarcoma. "Glioma" refers to predominantly brain-localized true tumors of the central nervous system (CNS) originating in the neuroglia, i.e. from the covering and supporting tissue of the nervous system that is derived from ectoderm. These gliomas are present in various stages of differentiation. Subtypes of glioma include spongioblastoma, oligodendroglioma, astrocytoma, glioblastoma, and retinoblastoma. In particular, the Glioblastoma multiforme (GBM) type of brain tumor is characterized by rapid growth and an extremely high rate of recurrence (i.e., a high percentage of patients experience brain tumor recurrence following surgical macroscopic excision).

Reactive gliosis is a space occupying lesion in the central nervous system (CNS), especially in the brain and the spinal cord, and is synonymous with "nonspecific gliosis", and comprises reactive astrocytes, or reactive neuroglia cells, which are GnRH-receptor positive. These lesions, called "gliotic lesions" or "gliosis lesions", occur mostly simultaneously at multiple sites within the central nervous system. "Reactive astrocytes" are astrocytes that become reactive in response to many CNS pathologies, including stroke, trauma, growth of a tumor or neurodegenerative disease. (*Neuroscience*, Volume 54, Issue 1, May 1993, Pages 15-36 Eddleston, M. and Mucke L. Molecular profile of reactive astrocytes—Implications for their role in neurological disease.) Reactive astrocytes occur prominently in response to all forms of central nervous-system injury or disease. The sources of reactive astrocytes appeared to be derived from proliferation, hypertrophy and hyperplasia (The Histochemical Journal, Volume 14, Number 2, March 1982. Ultrastructural Study of Enzymes in Reactive Astrocytes: Clarification of Astrocytic Activity. S. Y. A. Al-Ali and N. Robinson.). The gliosis lesions are considered a gliotic "scar". The process of astrocyte activation, identical for all forms of reactive astrocytes, results in nonspecific gliosis. (*Trends in Neurosciences*, Volume 17, Issue 4, 1994, Pages 138-142 Michael K. McMillian, Linda That, J-S. Hong, James P. O'Callaghan, Keith R. Pennypacker. Brain injury in a dish: a model for reactive gliosis). The diagnosis of "gliosis" is a pathological diagnosis typically made following resection of the gliotic lesion, or at least part of that lesion, e.g. by means of a brain biopsy (Waltregny A. et al. Contribution of stereotactic brain biopsies to the diagnosis of presenile dementia. *Stereotactic. Funct. Neurosurg.* (1990); 54-55: 409-412).

Malignant melanoma occurring in the CNS, primary or as metastasis, as well as malignant melanoma that primarily occurs in the skin, and/or malignant melanoma that disseminates (metastasizes) further in the skin and/or in other body organs, belong to a group of nervous system derived tumors; cf. Shamamian et al., 1994, Cancer Immunol. Immunother. 39, 73-83; Florenes et al., 1994, Cancer Research, 54, 354-356. Malignant melanomas are derived from the neuroectoderm, an embryonic layer. Burg et al., 1997, Deutsches Ärzteblatt 94, 890-895, describe a tumor growth inhibiting effect of Tamoxifen for malignant melanoma. Furthermore, glioblastoma and malignant melanoma have several tumor markers in common; cf. Shamamian et al., 1994, Cancer Immunol. Immunother. 39, 73-83; Florenes et al., 1994, Cancer Research 54, 354-356. In the case of metastases, the prognosis is quite poor; cf. Burg et al., 1997, Deutsches Ärzteblatt 94, 890-895.

Tumors originating in brain and/or nervous system and/or the meninges further comprise the neuroblastoma and the medullablastoma which, in their entirety, have been classified as the so-called primitive neuroectodermal tumors, abbreviated as PNET. These tumors further include the pinealoma, which originates in pineal body parenchyma and/or primordial germ cells in the pineal body region or the brain median. Moreover, the pineal body is associated with the origin of craniopharyngeoma (a tumor producing β-HCG or LH-like glycoprotein, respectively; cf. Tachibana et al., 1994, J. of Neurosurgery 80, 79-84), which is considered to be an ectodermal tumor and originates in the front/upper face of the pituitary.

For both craniopharyngeoma and meningeoma, which is considered to be a benign tumor originating in arachnoidal cover cells and often adhering firmly to the inner surface of the meninges (dura mater), the presence of progesterone receptors and estrogen receptors have been described. Furthermore, androgen receptors have also been established in the case of meningeoma. In clinical studies using anti-progesterone medicaments, tumor-shrinking effects have been observed.

Up to now, the investigation of alternative tumor therapies (different forms of chemotherapy, radiotherapy, etc.) in numerous clinical studies has failed to provide a substantial improvement of the prognosis for those tumors originating in the brain and/or nervous system and/or the meninges. At present, the standard therapy in the case of Glioblastoma multiforme consists of a complete as possible surgical excision of the tumor followed by conventional radiotherapy. Under this standard therapy protocol, the statistically reported mean survival time is 9-13 months, with individual variation and a slightly better prognosis for younger patients having been observed.

About 30% of patients with recurrent Glioblastoma multiforme show either a constant size or shrinking, respectively, of the inoperable residual brain tumor under sustained high-dosages of Tamoxifen, an anti-estrogen preparation. This tumor-inhibiting effect in glioblastoma treatment has not been attributed to its anti-estrogenic effect, but instead to its inhibition of protein kinase C (an intracellular signal mediator); cf. Puchner et al., Zentralblatt für Neurochirurgie, Supplement 1996, 47. Jahrestagung Deutsche Gesellschaft für Neurochirurgie, page 44; Pollack et al., 1995, The Efficacy of Tamoxifen as an anti-proliferative Agent in vitro for Benign and Malignant Pediatric Glial Tumors, Pediatr. Neurosurgery 22, 281-288). Moreover, Tamoxifen is known to increase the sensitivity of tumor cells for platinum-containing therapeutics as well as for radiotherapy.

For Glioblastoma multiforme (WHO grade IV astrocytoma) and for glioma with a lower grade of malignancy (WHO grade II-IV astrocytoma), steroid hormone receptors have been observed in a smaller percentage of the cases (cf. Paoletti et al., 1990, J. Neurosurgery, Characteristics and biological role of steroid hormone receptors in neuroepithelial tumors, 73, 736-742). Until now, an indirect anti-proliferative effect in the case of Glioblastoma multiforme and glioma grade II-IV has been observed in clinical studies in only about 30% of the cases via a response of the tumor to Tamoxifen administration (an anti-estrogen preparation).

Recently, several relatively reasonable new developments in Glioblastoma multiforme therapy have been described, although the prognosis quod vitam for patients with Glioblastoma multiforme remains poor due to the extremely high recurrence rate, despite the therapy regimens tried and tested so far, and also due to the lack of a specific therapy and early diagnosis. The oat-cell carcinoma, another malignant tumor, is frequently found in lungs and is also derived from neural cells (Tecimer et al Arch. Pathol. Lab. Med., 124, 520-525, 2000).

BRIEF SUMMARY OF THE INVENTION

The present invention relates to diagnostic methods which can detect the presence of GnRH receptors on tumor cells originating in brain and/or nervous system and/or the meninges and/or lungs and/or malignant melanoma and/or Kaposi sarcoma and/or reactive neuroglia cells and/or primitive neuroectodermal tumor cells, comprising contacting the cells with a ligand for a GnRH receptor and determining if binding has occurred.

Detection can be performed in an early growth stage of the tumor, thereby reducing any time delay in surgically removing the tumor and the onset of any post-operative treatment.

In one embodiment, the invention relates to a method for detecting GnRH receptors on malignant cells of a tumor originating in brain and/or nervous system and/or the meninges and/or Kaposi sarcoma and/or oat-cell carcinoma and/or reactive neuroglia cells and/or primitive neuroectodermal tumor cells. In another embodiment, the invention relates to a method for determining the relative number of GnRH receptors. The invention is further directed to providing a diagnostic kit for detecting GnRH receptor on tumor cells of tumors originating in brain and/or nervous system and/or the meninges and/or reactive neuroglia cells and/or primitive neuroectodermal tumor cells and/or of Kaposi sarcoma, comprising a ligand for a GnRH receptor and a means for detecting bound ligand. The means for detecting bound ligands are known to a person skilled in the art and may comprise immunohistochemical staining methods and/or fluorescent or radioactive labels. The labels may be conjugated ligand and/or to antibodies directed against ligand and/or GnRH receptor.

The ligand of a GnRH receptor comprises a chemical compound, and/or an antibody, and/or a hormone, and/or a GnRH agonist and/or a GnRH antagonist and/or a functional part and/or derivative thereof, e.g. a peptide analogue of GnRH having features in common with the amino acid composition of the GnRH parent molecule, which binds to a GnRH receptor. The agonist activity of GnRH peptide analogues is well-known to be attributed to such structural features as the [R]amino acid replacements at the $6^{th}$ position together with aza-amino acid replacements at the $10^{th}$ position, or substitution of the $Gly_{10}$-$NH_2$ residue by an ethylamide group in the parent GnRH peptide molecule; exemplary GnRH peptide agonists are shown in TABLE I. These modifications yield agonist analogues that are 100-200 times more potent than the parent peptide GnRH (Hoitink, M., Stability of Gonadorelin and Related Compounds, dissertation, University of Utrecht, Jun. 8, 1998, Chapter 1, Page 15), and the functional agonist activity on the GnRH receptor is directly related to structural features known to one of ordinary skill in the art. Replacement of the $6^{th}$ amino acid position in GnRH, or e.g. in GnRH II at the $6^{th}$ amino acid (glycine) with lysine produces a GnRH peptide analogue called "(D-Lys6)-GnRH" or "(D-Lys6)-GnRH II" having GnRH agonist activity at the GnRH receptor. The (D-Lys6) moiety is known as a "spacer" molecule that facilitates the formation of chemical conjugates with other molecules, e.g. with other peptides or proteins, that can exhibit apoptotic activity. The (D-Lys6) moiety may also facilitate conjugation with molecules that are activated under hypoxic cellular conditions, with drugs that inhibit cellular division, cause apoptosis, or have other cytotoxic activity that completely kills the cell.

A "functional part of a protein" is defined as a part which has the same kind of qualitative biological properties, but not necessarily in amount. By "biological properties" is meant the capability to bind to GnRH receptor. A "functional derivative of a protein" is defined as a protein which has been altered such that the biological properties of the molecule are essentially the same in kind, not necessarily in amount. A derivative can be provided in many ways, for instance through conservative amino acid substitution.

A person skilled in the art can generate analogous compounds of a protein. This can, for instance, be done through screening of a peptide library. Such an analogue has essentially the same qualitative biological properties of the protein, but not necessarily in amount. An "agonist of a GnRH receptor" comprises a chemical compound, and/or an antibody, and/or a hormone and/or a functional part and/or derivative thereof which combines with a GnRH receptor on a cell to initiate a physiological response in the cell as if the receptor had been actually activated by GnRH. An "antagonist of a GnRH receptor" comprises a chemical compound, and/or an antibody, and/or a hormone and/or a functional part and/or derivative thereof which combines with a GnRH receptor on a cell and, at least partially, prevents a physiological response in that cell.

The invention also provides a method of decreasing cellular replication of such tumors, which results in a better prognosis for patients suffering from such a tumor. In one embodiment, the invention relates to a method for decreasing cellular replication of GnRH-positive glioma, oat-cell carcinoma, malignant melanoma, reactive neuroglia cells, primitive neuroectodermal tumor cells or Kaposi sarcoma, comprising administering to a cell, a replication decreasing amount of a GnRH agonist. In another embodiment, cellular replication is decreased in a patient suffering from the tumor. Therefore, the invention also provides for a method for decreasing cellular replication of GnRH-positive glioma, oat-cell carcinoma, malignant melanoma, reactive neuroglia cells, primitive neuroectodermal tumor cells or Kaposi sarcoma comprising administering to a subject a replication decreasing amount of a GnRH agonist. In another embodiment, cellular replication is even further decreased by combining the replication decreasing ability of GnRH agonist with a cytotoxic substance. In yet another embodiment of the invention, the cytotoxic substance is coupled to the GnRH agonist.

In one embodiment of the invention, the cytotoxic substance is coupled to the GnRH agonist (D-Lys6)-GnRH. In typical peptide nomenclature, the occurrence of (D-Lys6) before the GnRH indicates that the usual amino acid group at the 6-position of the GnRH molecule (i.e., a glycine or "Gly" group), has been replaced by lysine (or "Lys"). This observation is equally applicable for the molecule (D-Lys6)-GnRH II, such that instead of glycine, the 6-position amino acid is lysine. Additionally, (D-Lys6)-GnRH II is a preferred GnRH agonist for coupling with, for example, other peptides or with proteins or molecules that are activated under hypoxic cellular conditions. Another GnRH analogue suitable for use with the present invention is (D-Lys6)-Lamprey-GnRH II, wherein the "Gly" located at the 6-position of the wild-type Lamprey GnRH II molecule is replaced by lysine ("Lys"). (D-Lys6)-Lamprey-GnRH II has not been described until now, however, Lamprey-GnRH II is known (Scott et al. (2008) Endocrinology 149(8): 3860-3869).

The direct anti-proliferative effect of GnRH agonist application on brain-derived tumors, e.g. Glioblastoma multiforme, has not been described to date. It has also been unconfirmed that GnRH receptors are actually present on human ectodermal tumors, including Glioblastoma multiforme. Furthermore, it has been also been unknown, until present that GnRH receptors actually exist on Kaposi sarcoma.

The present invention contributes to an improvement in both the diagnosis and therapy of tumors originating in brain and/or nervous system and/or the meninges and/or reactive neuroglia cells and/or primitive neuroectodermal tumor cells and/or Kaposi sarcoma and/or oat-cell carcinoma, by providing a suitable biological target for said diagnosis and therapy strategies.

The present invention is further directed to the use of diagnostic kits for the detection of GnRH receptors in the area of immunohistological diagnostics and/or for the detection of GnRH receptor mRNA for monitoring of a tumor therapy regime, aftercare for early recurrence detection during follow-up of the residual tumor still present after operation, for example a low grade glioma (G II-III WHO; cf. World Health Organization (WHO) classification of tumors of the central and peripheral nervous system, in: Kleihues et al., 1993, Histological Typing of Tumors of the Central Nervous System, Springer Verlag, Berlin-Heidelberg, New York-Tokyo), or for the detection of malignancy in the sense of a Glioblastoma multiforme (G IV), and for early detection in risk groups by screening for the presence of tumors, such as Glioblastoma multiforme, originating in brain and/or nervous system and/or the meninges.

The kit according to the present invention may be used to detect GnRH receptors on cell membranes or in body fluids, such as blood, plasma, serum, urine or liquor, tissue extracts, tissue liquids, in vitro cell culture supernatants and cell lysates. The GnRH receptor may be determined immunohistochemically on, for example, operatively excised tumor preparations or tissue cultures or, by means of a conventional radioimmunological assay, for example, in body fluids. The diagnostic kit comprises a GnRH agonist and/or a GnRH antagonist and/or a monoclonal or polyclonal antibody against human GnRH receptors and/or one or more specific primers against GnRH receptors, for example, for the amplification of the cDNA of a GnRH receptor in a reverse transcriptase-polymerase chain reaction (RT-PCR). Detection of GnRH receptors is conducted using well known immunological assays, in particular through the use of enzyme-linked immunoadsorbent assays (ELISA), or by using the methods disclosed herein for the detection and determination of GnRH receptors on degenerated cells.

DETAILED DESCRIPTION OF THE INVENTION

Figure 1:
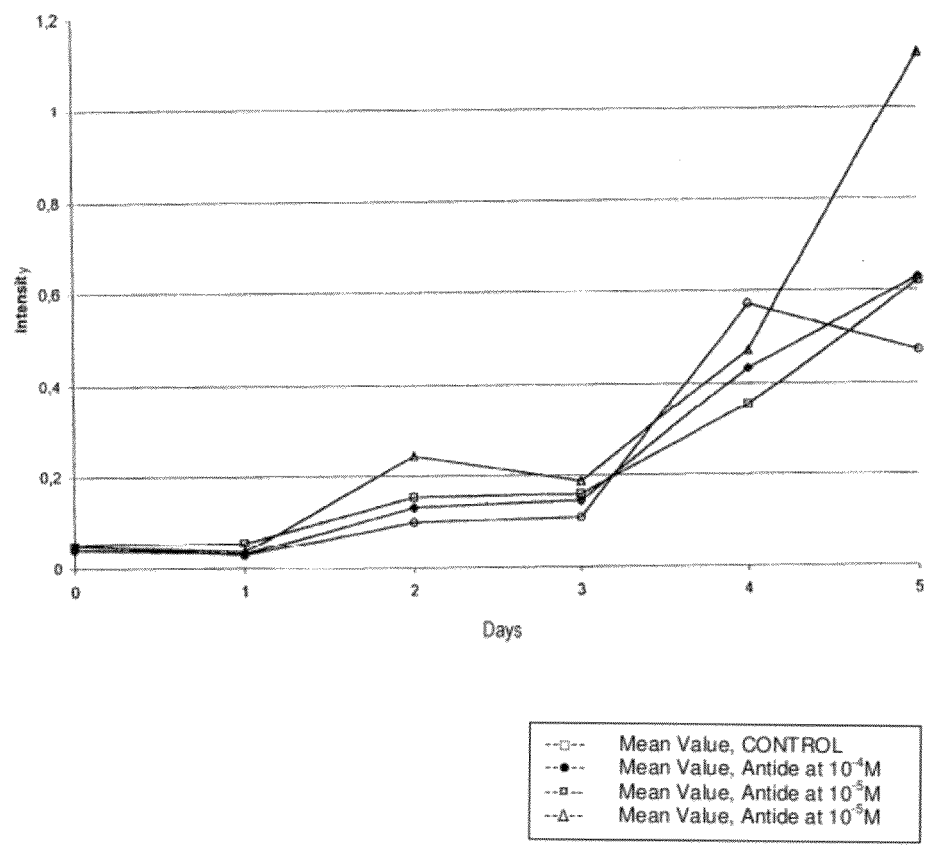
FIG. 1: Inhibition of proliferation on malignant melanoma MV3 cells by Antide® (GnRH antagonist).

In one embodiment, the present invention relates to a method for the detection and/or determination of GnRH receptors on degenerate cells of a tumor originating in brain and/or nervous system and/or the meninges comprises the following steps of: a) homogenizing peroperatively obtained tumor tissue, b) separating the membrane fraction, c) determining the protein concentration in the membrane fraction of b), and d) determining the concentration of GnRH receptors in the membrane fraction of b). The present method is particularly useful for the detection and/or quantification of GnRH receptors in tissue derived from Glioblastoma multiforme, medulloblastoma, pinealoma, neuroblastoma, craniopharyngeoma, meningeoma, chordoma, Ewing sarcoma, malignant melanoma, oat-cell carcinoma, reactive neuroglia cells, primitive neuroectodermal tumor cells, or Kaposi sarcoma, which can be additionally useful in the diagnosis of tumors.

In another embodiment, fresh human tumor tissue is collected, for example during a brain tumor surgery procedure (i.e. "preoperatively"), followed by storage in liquid nitrogen. For GnRH receptor determination, these frozen tissue samples are ground and homogenized. In a centrifugation step, the samples are separated from larger tissue debris. The supernatant is again centrifuged. The resulting sediment (pellet) contains the membrane fraction which is subject to further homogenization in order to obtain an optimally homogenous membrane suspension. The membrane suspension is then used in a radio receptor assay for determining GnRH receptors as follows. First, the protein concentration in the prepared membrane fraction is determined photometrically using conventional methods, e.g. the BioRad protein assay (BioRad, Munich). Determination of the GnRH receptor concentration is carried out using a known GnRH agonist, such as Buserelin, which can bind specifically to GnRH receptors in the prepared membrane fraction. Since the GnRH agonist has been radiolabeled, for example using $^{125}I$, the concentration of bound radiolabeled GnRH agonist mirrors the concentration of GnRH receptors in the obtained membrane fraction. The concentration of bound radiolabeled GnRH agonist is determined by means of radioactive counts per minute (cpm). Both low affinity/high capacity and high affinity/low capacity GnRH receptor binding sites are evaluated (cf. Baumann, K., et al., 1993, Breast Cancer Research Treatment, vol. 25, page 37-46).

GnRH receptors as well as GnRH agonist treatment has, until now, never been described for any of the following tumor types: craniopharyngeoma, meningeoma, oat-cell carcinoma, chordoma, Ewing sarcoma, malignant melanoma, reactive neuroglia cells, primitive neuroectodermal tumor cells or Kaposi sarcoma. For these particular tumor types, no blood-brain barrier exists, since they are originally extracerebral, intracranial or peripheral tumors. Therefore, the therapy according to the present invention, which describes the use of GnRH agonists or conjugates thereof to treat these tumor types, is very advantageous. However, the blood-brain-barrier is permeable for GnRH since a two-direction-system, a bi-directional active transport of GnRH across the blood-brain-barrier exists (Barrera, C., Banks, W. A., Fasold, M. B., and Kastin, A. J., 1991, Effects of Various Reproductive Hormones on the Penetration of LHRH Across the Blood-Brain Barrier, Pharmacology, Biochemistry & Behaviour, vol. 41, 255-257). Accordingly, the present therapies using GnRH agonists have advantages over treatment using Tamoxifen for which a blood-brain-barrier does exist. For Ewing sarcoma and other peripheral forms of PNET outside of the nervous system, for malignant melanoma and for Kaposi sarcoma, the blood-brain-barrier does not typically play an essential role in the treatment with GnRH agonists, since these tumors usually arise from and stay external to the blood-brain-barrier.

The invention further relates to a method for decreasing cellular replication of GnRH-positive glioma, oat-cell carcinoma, malignant melanoma, reactive neuroglia cells, primitive neuroectodermal tumor cells or Kaposi sarcoma comprising administering to a cell a replication decreasing amount of a GnRH agonist. In particular, the invention relates to a method for decreasing cellular replication of GnRH-positive glioma, oat-cell carcinoma, malignant melanoma, or Kaposi sarcoma, comprising administering to a subject a replication decreasing amount of a GnRH agonist. In one embodiment, the method for decreasing cellular replication of GnRH-positive glioma, oat-cell carcinoma, malignant melanoma, or Kaposi sarcoma additionally comprises administering a cytotoxic substance, such as a radioisotope, or another toxic substance such as ricin A or the like. The cytotoxic substance is preferably coupled or conjugated to the GnRH agonist.

TABLE I

The following is an exemplary listing of GnRH agonists having the chemical structure of [R]-amino acid replacements at the $6^{th}$ position together with aza-amino acid replacements at the $10^{th}$ position, or substitution of the $Gly_{10}$-$NH_2$ residue by an ethylamide group in the parent GnRH peptide molecule and exemplary GnRH antagonists which are suitable for the treatment of a tumor having GnRH receptors and originating in brain and/or nervous system and/or the meninges and/or reactive neuroglia cells and/or primitive neuroectodermal tumor cells and/or of Kaposi sarcoma:

| GnRH AGONISTS: Pharmacological substance name | GnRH ANTAGONISTS: Pharmacological substance name |
|---|---|
| Leuprorelinacetate, Leuprorelin | Ac-D-Nal(2)-D-4-Cl-Phe-D-Pal- |
| Goserelinacetate, Goserelin | Ser-1-MePal-D-IsopropylLys-Leu- |
| Triptorelinacetate, Triptorelin | IsopropylLys-Pro-D- |
| Buserelinacetate, Buserelin | AlaNH$_2$ (ANT 135-25) |
| Nafarelinacetate, Nafarelin | Cetrorelix |
| Azagly-Nafarelinacetate, | Antide |
| Azagly-Nafarelin | Abarelix |
| Histrelinacetate, Histrelin | Ozarelix (D-63153) |

TABLE I-continued

The following is an exemplary listing of GnRH agonists having the chemical structure of [R]-amino acid replacements at the 6$^{th}$ position together with aza-amino acid replacements at the 10$^{th}$ position, or substitution of the Gly$_{10}$-NH$_2$ residue by an ethylamide group in the parent GnRH peptide molecule and exemplary GnRH antagonists which are suitable for the treatment of a tumor having GnRH receptors and originating in brain and/or nervous system and/or the meninges and/or reactive neuroglia cells and/or primitive neuroectodermal tumor cells and/or of Kaposi sarcoma:

| GnRH AGONISTS: Pharmacological substance name | GnRH ANTAGONISTS: Pharmacological substance name |
|---|---|
| Lutrelinacetate, Lutrelin | Acyline |
| Deslorelinacetate, Deslorelin | Azaline B |
| Cystorelin | Teverelix |
| Gonadorelin, GnRH | Degarelix |
| Zoladex | (2S)-2-[5-[2-(2- |
| Decapeptyl | azabicyclo[2,2,2]oct- |
| (D-Lys6)-GnRH | 2-yl)-1,1-dimethyl-2-oxoethyl]- |
| (D-Lys6)-GnRH II | 2-(3,5-dimethylphenyl)-1H-indol- |
| Lamprey-GnRH II | 3-yl]-N-(2-pyridin-4-ylethyl-) |
| Lamprey GnRH III | propan-1-amine (or "IN3") |
| | Nal-Glu |
| | Orntide |
| | 4-[[(1R)-2-[5-(2-Fluoro-3-methoxyphenyl)-3-[[2-fluoro-6 (trifluoromethyl)phenyl]methyl]-3,6-dihydro-4-methyl-2,6-dioxo-1(2H)-pyrimidinyl]-1-phenylethyl]amino]butanoic acid (or "Elagolix" or "NBI-42902") |
| | 1-[7-Chloro-3-(3,5-dimethyl-phenyl)-2-oxo-4-(2-piperidin-2-yl-ethoxy)-1,2-dihydro-quinolin-6-yl]-3-pyridin-2-yl-urea |
| | 3-[Benzyl-methyl-amino)-methyl]-2-tert-butyl-8-(2-fluoro-benzyl)-6-(3-methoxyphenyl)-7-methyl-8H-imidazo[1,2-a]pyrimidin-5-one |
| | NOX 1255 |
| | CMPD1 |
| | TAK-013 |
| | Ramorelix |
| | Antarelix |

The minimum treatment dosage for each of the GnRH agonists in TABLE I corresponds to the dosage cited in the ROTE LISTE® for other indications of use for the subcutaneous or the intramuscular administration forms of each compound, respectively. For the intravenous administration of GnRH agonists, the minimal daily dose is used; cf. for example Klijn et al., 1982, The Lancet, 1213-1216.

According to the invention, GnRH agonists may be used in any suitable form. For tumors within the blood-brain-barrier, direct injection, e.g. into the circulation, intra-arterially directly into the nervous system circulation, intravenously, injection or local application to the tumor bed following surgery, directly after macroscopic tumor resection, peroperatively or using am OMMAYA® reservoir, or another form of subcutaneous ventricular injection is preferred. It is possible to use both GnRH agonists because both bind as ligands to the GnRH receptor. Furthermore, ligands which are specifically directed to the GnRH receptor may be used, for example, human or humanized antibodies. In most cases, it is preferable to ensure that the targeting agent primarily reaches tumor cells. Therefore, imaging methods using the ligand with tracers are a further aspect of the present invention. If the ligand is localized mainly in the tumor, the ligand may be coupled to a cytotoxic agent, such as a radioisotope or another toxic substance including ricin A. Preferred GnRH agonists suitable for use in the present methods are cited in the ROTE LISTE® which is explicitly incorporated herein by reference (ROTE LISTE® 1997, paragraph 50, part 3, pituitary hormones, 50038 to 50056, editor ROTE LISTE® Service GmbH, Frankfurt/Main).

The above-mentioned GnRH agonists may also be administered in dosages that are approved for other treatments. Other appropriate dosages may be established during dose determination studies for the use of similar materials (i.e. substances, medicaments) including somatostatin analogues in pituitary adenoma, glioblastoma or pancreas adenocarcinoma, or for Phase II studies with GnRH analogues (agonists or antagonists) for other indications, for example, mammary carcinoma, prostate carcinoma or ovarian carcinoma.

In a particular embodiment, the GnRH agonists are conjugated with a gonadotropin or LH inhibitor, respectively, such as Gossypol (cf. Flack et al., 1993, J. Endocrinol. Metab., Oral Gossypol in the Treatment of Metastatic Adrenal Cancer 76, 1019-1024; Poso, H., et al., The Lancet, 1980, 885) or with melatonin or a melatonin analogue (an agonist or antagonist) (cf. Lissoni et al., 1996, Increased Survival Time in Brain Glioblastomas by a Radioneuroendocrine Strategy with Radiotherapy plus Melatonin Compared to Radiotherapy Alone, Oncology 53, 43-46).

In the following, an exemplary method embodiment is described.

Using a radio receptor assay, the present invention defines for the first time the presence and concentration of GnRH receptors in cell membranes derived from human brain or nervous system tumor cells, i.e. membrane GnRH receptors that are effective in vitro. According to the present methods, the biological activity, or specifically the active GnRH receptors, respectively, is determined. For this purpose, radiolabeled Buserelin, a GnRH agonist, is used as a marker because it specifically binds to GnRH receptors. Based on the observed cpm for bound Buserelin, the GnRH receptor concentration may be determined. This detection technique has been used to assess GnRH receptors on other tumor types such as mammary carcinoma. The present methods also provide for the measurement of GnRH receptor concentration on cell membrane extracts derived from fresh human tumor tissue.

The present invention provides for obtaining tissue during preoperative resection of the tumor, and processing same for pathological anatomical examination and for GnRH receptor determination. Following pathological anatomical examination and confirmation of the histological diagnosis of a tumor originating in brain and/or nervous system and/or the meninges and/or reactive neuroglia cells and/or primitive neuroectodermal tumor cells and/or of Kaposi sarcoma, a prognosis may be determined for therapy success during the course of treatment with the GnRH agonists, GnRH antagonists and combinations and conjugates thereof, following an evaluation of the concentration of GnRH receptors that are present.

At a concentration of the GnRH receptor of more than 1000 amol/mg (=1 fmol/mg) membrane protein, a patient will be diagnosed as GnRH receptor-positive. Being not GnRH receptor-positive is not an established criterion for exclusion from treatment, since there are presently no existing clinical exclusion criteria for receiving GnRH agonist treatment. Whether a patient is GnRH receptor-positive is judged prognostically as a faster tendency of recidivation than that of being GnRH receptor-negative in the course of tumor growth under standard treatment paradigms, wherein the GnRH receptor functions as a prognostic tumor marker. Also, being GnRH receptor-positive is considered to be particularly advantageous for the treatment with GnRH agonists. Moreover, being GnRH receptor-positive or -negative provides useful information regarding the prognosis of expected therapy success such that the GnRH receptor acts as a prognostic tumor marker in that treatment. The GnRH agonist treatment is started immediately after pathological anatomical examination, e.g. postoperatively in the case of rapid section pathological diagnostics.

Following the determination of GnRH receptor presence, a suitable ligand (GnRH agonist or a conjugate) is selected and administered to the patient from whom the tumor was derived, preferably after diagnostic imaging methods. Cf. MTT test literature: Hunter et al., 1993, Europ. J. Surg. Oncology, 242-249.

The treatment is continued as long as no complete remission has occurred. Criteria for judging the therapeutic effectiveness are: (A) tumor volume on MRT images and/or CAT scan images, (B) recidivation-free survival, (C) overall survival for initial application, and (D) Karnofsky and Spitzer indices. The dosage for administration, which may be in any suitable form known to those skilled in the art, is presently described.

The precise mechanism of action of GnRH agonists on tumors is unknown. For the tumor types known to bear active GnRH receptors, such as mammary carcinoma, prostate carcinoma and ovarian carcinoma, a locally regulatory autocrine-paracrine system of action has been proposed in the literature; cf. Irmer et al., 1995, Cancer Research 55, 817-822. For the tumors mentioned, anti-proliferative activities of GnRH agonists or GnRH antagonists have been described in the literature, both in vitro (Palyi et al., 1996, Cancer Detection and Prevention, 20, 146-152; Irmer et al., 1995, Cancer Research, 55, 817-822; Pati et al., 1995, Endocrinology, 136, 75-84) and in vivo, or clinically, respectively; cf. Gonzalez-Barcena et al., 1994, The prostate 24, 84-92; Jonat et al., 1995, European J. of Cancer, 31A, 137-142; Emons and Schally, 1994, Human Reproduction Update 9, No. 7, 1364-1379; wherein this observed anti-proliferative activity goes beyond the expected anti-proliferative effects associated with reversible "chemical castration" by GnRH agonists.

For glioblastoma and glioma, a similar mechanism of action could be considered. In the literature, (Constam et al., 1992, J. Immunology, 148, 1404-1410) the production of transforming growth factor $\beta$ (TGF-$\beta$) by glioblastoma cells has been described. Growth factor TGF-$\beta$ has been described by Melcangi et al., 1995, Endocrinology, 136, 679-686, as a product of rat glia cells, i.e., normal non-tumor cells, which has been shown to stimulate the natural GnRH production in hypothalamic cells in vitro. It has been postulated that GnRH produced and secreted locally by glioblastoma cells has a stimulating effect on the tumor growth, which has also been observed for TGF-$\beta$. Furthermore, human glioblastoma cells and glioma cells, respectively, are also able to secrete circulating immunosuppressive substances, mainly TGF-$\beta$, and therefore may induce an adverse effect on cellular immune reactions. Besides a GnRH-stimulating function, the observed increase in TGF-$\beta$ presumably also has an immunosuppressive (defense inhibiting) effect on the cellular immunity of the patient due to which tumor growth is promoted and tumor size increases. For Glioblastoma multiforme, medulloblastoma, and malignant melanoma, this immunosuppressive phenomenon of TGF-$\beta$ has been described; cf. Stockhammer et al., 1995, J. of Neurosurgery 83, 672-681; Jennings et al., 1994, Hum. Pathol. 25, 464-475; Bizik et al., 1996, J. Cell Biochem. 62, 113-122; van Belle et al., 1996, Am. J. Pathol. 148, 1887-1894. This autocrine-paracrine growth regulating system may be reversed, thus resulting in a decrease in tumor size. This reversion (also referred to as "negative feedback" in the field of endocrinology) may be, in principle, affected by an excess of GnRH (competitive inhibition). This effect is even enhanced by using GnRH agonists or GnRH antagonists instead of GnRH. A result of this therapy is a decrease in TGF-$\beta$ production followed by a decrease in tumor size resulting therefrom. $\beta$-HCG also plays an immunosuppressive role. According to the invention, the LH-$\beta$ and $\beta$-HCG production, respectively, are also inhibited by GnRH agonists or GnRH antagonists. Additionally, in GBM the EGF production is inhibited.

For the tumors originating in the brain and/or nervous system and/or the meninges according to the instant invention, reference is made to the World Health Organization (WHO) classification of tumors of the central nervous system which has been established in 1990 (Kleihues et al., 1993, Histological Typing of Tumors of the central nervous system, Springer Verlag, Berlin Heidelberg New York Tokyo). In addition to the tumors cited in this WHO classification, malignant melanoma, Ewing sarcoma, reactive neuroglia cells, primitive neuroectodermal tumor cells and the Kaposi sarcoma are also contemplated by the present invention. Excluded from the present invention are the pituitary adenoma, all metastases except Ewing sarcoma, melanoma and Kaposi sarcoma, lymphomas and hematopoietic tumors. Germ cell tumors, such as chorion carcinoma, are similar to malignant tumors of the placenta which are known for bearing GnRH receptors. Therefore, the germ cell tumors of the central nervous system belong to the present invention. The Kaposi sarcoma with multicentric occurrence in the body consists of cells of monoclonal origin (Rabkin et al., 1996, The New England Journal of medicine, 14, 988-993). It has specific antigens in common with skin neurofibroma, a tumor originating in the nervous system (Rudolph, P., et al., 1997, Am. J. Surg. Pathol. (US), 21(7), 791-800).

With respect to hormones and hormone receptors expressed by these tumor types, Kaposi sarcoma is similar to malignant placental tumors and meningeoma, since Kaposi sarcoma also expresses $\beta$-HCG receptors and exhibits an anti-proliferative response to the administration of $\beta$-HCG like, for example, meningeoma cells (Boyle-Wash et al., 1995, Effect of glycoprotein and protein hormones on human meningeoma cell proliferation in vitro, Journal of Endocrinology, 145, 155-161; Albini et al., 1997, The beta-core fragment of human chorionic gonadotropin inhibits growth of Kaposi sarcoma-derived cells and a new immortalized Kaposi sarcoma cell line, AIDS (US), 11(6), 713-721; Gill et al., 1996, The effects of preparations of human chorionic gonadotropin on AIDS-related Kaposi sarcoma, The New England Journal of Medicine, 335 (17), 1261-1269). Analogous to meningeoma, Kaposi sarcoma expresses GnRH receptors, wherein the observed autocrine connection of GnRH being known as the $\beta$-HCG releasing hormone in placenta and placental tumors plays a role (Lin et al., 1995, J. Clin. Endocrinol. Metab. 80, 580-585). The tumors referred to in the above-mentioned WHO classification of central nervous system tumors, as well as malignant melanoma, with $\beta$-HCG production and/or $\beta$-HCG receptors do carry GnRH receptors. The Ewing sarcoma belongs to the group of primitive neuroectodermal tumors (PNET) and is a peripheral form thereof (Grier, H. E., 1997, The Ewing Family of Tumors. Ewing sarcoma and primitive neuroectodermal tumors. Pediatric Clin. North Am. (US), 44 (4), 991-1004).

The pineal gland (Glandula pinealis) is the origin of the production of the hormone melatonin, which is a GnRH receptor expression stimulating hormone in metastasizing prostate carcinoma in the case of resistance during a GnRH agonist treatment (cf. Lissoni et al., 1997, European Urology 31, 178-181), and in addition has an anti-angiogenetic activity (Regelson, W., Pierpaoli, W., 1987, Cancer Invest., 5, 379-385). GnRH agonists and GnRH antagonists have an anti-mitotic and anti-proliferative activity, respectively, by inhibiting growth factors such as epidermal growth factor (Motta et al., 1996, J. Steroid Biochem. Molec. Biol., 56, 107-11, 1996). Epidermal growth factor is also present as a mitogen and, thus, as a positive growth factor, e.g., in Glioblastoma multiforme (Rao et al., 1996, Peptides (US), 17, 179-181). Accordingly, a melatonin-GnRH analogue conjugate reasonably combines an anti-mitotic and anti-angiogenetic activity on tumors, such as glioblastoma, and induces further expression of GnRH receptors, e.g. in Glioblastoma multiforme, in order to avoid resistance against GnRH agonist/GnRH antagonist treatment due to GnRH receptor depletion.

According to the present invention, there are provided for the first time GnRH agonists for treating tumors originating in brain and/or nervous system and/or the meninges and/or reactive neuroglia cells and/or primitive neuroectodermal tumor cells and/or of Kaposi sarcoma.

According to the present invention, the GnRH agonists as well as the conjugated GnRH agonists are used to treat tumors originating in brain and/or nervous system and/or the meninges, for example Glioblastoma multiforme. These compositions, according to the present invention, may be prepared in any manner known to the skilled artisan, in particular for subcutaneous, intramuscular, intravenous, intraspinal or subdural, respectively, or intranasal application or in the form of a sustained release implantation. The medicaments according to the present invention may also be administered via a subcutaneous ventricular cytostatic reservoir being connected to a cerebral ventricle wherein the reservoir may be replenished by injections through the skin. The GnRH agonists may be administered in the same dosage as those which are for example used in the treatment of prostate, mammary carcinoma or endometriosis; cf. e.g. ROTE LISTE®, 1997, paragraph 50, part 3, hypothalamic hormones, 50038 to 50056, Editor ROTE LISTE® Service GmbH, Frankfurt/Main, which is included herein explicitly by reference. The minimal dose corresponds to the dose cited in the ROTE LISTE® for the respective GnRH agonists. For example, in the case of intraspinal or subcutaneous ventricular administration via a cytostatic reservoir, the minimal dosage may be lower than that cited in the ROTE LISTE® for the respective GnRH agonists. The maximal dose corresponds to the $LD_{50}$ value for the respective GnRH agonists. The dosage may be optionally increased or decreased following a finding of the GnRH receptor concentration obtained in a neurological manner. The frequency of application or daily dose, respectively, may also be found in the ROTE LISTE®. Preferably, the medicaments are administered until complete remission (regression) of the tumor which may be evaluated both neuroradiologically and clinically.

For subcutaneous administration, e.g. CARCINIL®, DECAPEPTYL® 0.5 mg/0.1 mg or Uno-Enantone may be employed. As sustained release implantations for example PROFACT®-DEPOT, ZOLADEX®, or Enantone Monatsdepot may be administered. For intramuscular administration, e.g. DECAPEPTYL®-DEPOT, DECAPEPTYL®-GYN, or Enantone-Gyn may be employed. For intranasal administration e.g. PROFACT®-NASAL, SUPRECUR®-NASAL, OR SYNARELA®-NASAL may be used. For intravenous administration or intranasal administration, respectively, for example PROFACT® PRO INJECTIONE/-NASAL may be administered in the dosage specified by Klijn, J. G., and De Jong, F. H. in Klijn, J. G., and De Jong, F. H., 1982, The Lancet, 1213-1216.

Various aspects of the present invention are illustrated in the following Examples, which are provided for the purposes of illustration and are not intended in any way to limit the scope of the present invention

EXAMPLES

Example 1

Determination of the Concentration of GnRH Receptors

One method for determining the concentration of GnRH receptors in cell membrane extracts that are derived from various cell lines and/or cell cultures is the Decapeptyl® radio receptor assay (described by Emons, G., et al., 1993, Cancer Research 53, 5439-5446). According to this protocol, GnRH receptor concentration is determined on a human cell line, such as the human glioblastoma cell line U-87 MG or U-373MG (Pinski et al., 1994, Cancer Research 54, 5895-5901). In this assay, the low affinity/high capacity as well as the high affinity/low capacity GnRH receptor binding sites are evaluated. Significant anti-proliferative effects were observed in these particular cell lines, similar to effects previously shown for the cell lines EFO-21 and EFO-27 (Emons, G., et al., supra).

Another method for determining GnRH receptor concentration on cell membrane extracts of cell lines and/or cell cultures is the LHRH radio receptor assay using labeled Triptorelin® (Emons, G., et al., supra). This assay can be performed on a Kaposi sarcoma cell line such as the well-known cell line KSY-1 or KS-SLK (Parkash et al., 1996, New England Journal of Medicine 335, 17, 1261-1269) and on a human malignant melanoma cell line such as MV3 and BLM (Goldbrunner, R. H., et al., 1996, Anticancer Research 16 (6B), 3679-3687) to obtain the GnRH receptor determinations (see Emons, G., et al., supra, for GnRH determinations made on the EFO-21 and EFO-27 cell lines).

Characterization of Ligands of the GnRH Receptor (GnRH-R) Isoforms on Glioblastoma Cells.

Cultured glioblastoma cells are washed with buffer and completely lysed under conditions that suspend all membrane proteins. This requires the addition of mild detergents (e.g. NP40). Next, the suspension is mixed with a lysate of cells or tissue, in which the ligand is to be detected. The cells may originate from hypothalamic tissue or from a tumor or from cultured cells thereof. Next an antibody, which is specifically directed against the GnRH receptor (GnRHR), is added to form a complex with the GnRH receptor and the ligand. The monoclonal anti-GnRHR antibody, as published by Karande et al., is used for this purpose. Next, the antibody, GnRHR and ligand complex is purified from the solution by adding solid beads coupled to Protein G (e.g. Protein G Sepharose from Pharmacia) followed by a short centrifugation. The proteins of the bead-coupled complex of Protein G, GnRHR and ligand is then separated by electrophoresis or chromatography. The bands of the electrophoretic gel or the eluted peaks of the chromatography are then characterized. For this, standard methods such as protein sequencing and/or mass spectroscopy are suitable. The resulting sequence or the determined exact mass is compared with the data of known proteins using standard databases, resulting in the identification of the yet unknown ligand that is bound to the GnRHR.

Example 2

Determination of the mRNA of GnRH Receptors by Means of RT-PCR

One method for determining GnRH receptor messenger RNA is by means of reverse transcriptase polymerase chain reaction (RT-PCR). For example, in a first reaction, RNA derived from the glioblastoma cell line U-87 MG or U-373MG is transcribed to cDNA. In a further reaction, for example, the 884 bp fragment of the pituitary GnRH receptor (Kakar, S., et al., Biochem. Biophys. Res. Comm., 1992, 289-295) or of the placental GnRH receptor (Leung, P. C. K., Biological Signals, 1996, 5, 63-69) or of the placental GnRH receptor gene (Lin, L., et al., J. Clinical Endocrinol. Metabolism, 1995, vol. 80, No. 2, 581-584) is amplified using specific primers in a RT-PCT, wherein the cDNA of a known GnRH receptor-positive cell line serves as the positive control. Then, the reaction products are visualized in a polyacrylamide (PAA) gel. On the PAA gel, it can be observed: in lane 1, the fragment length marker; in lane 2, a clear band of the 884 bp GnRH receptor PCR product in the MCF 7 positive control; in the lane for the glioblastoma cell line, a signal for an 884 bp product or other GnRH receptor splice variant (fragment) signals results. This mRNA detection procedure is performed in a manner similar to other GnRH receptor mRNA determination assays; see, for example Irmer et al., 1995, Cancer Research, 55, 817-822.

Example 3

Therapeutic In Vitro Study

Proliferation Assay on Cell Cultures

A human cell line, such as the well known human glioblastoma cell lines U-87MG or U-373MG (Pinski et al., supra), or a human cell line such as the well known Kaposi sarcoma cell lines KSY-1 or KS-SLK (Parkash et al., 1996, New England Journal of Medicine, 335, 17, 1261-1269), or a human cell line such as the well known human malignant melanoma cell line MV3 or BLM (Goldbrunner, R. H., et al., 1996, Anticancer Research 16 (6B), 3679-87), or a human medulloblastoma cell line such as the well known cell line Daoy or D283 MED (Stockhammer et al., 1995, J. Neurosurgery, 83, 672-681), or human meningeoma cell cultures (Boyle-Wash, E., et al., 1995, Journal of Endocrinology, 145, 155-161), are cultured as previously described for the above-mentioned cell lines and then treated with a concentration of the GnRH agonist Triptorelin®, GnRH antagonist SB-75 (Cetrorelix®) or GnRH antagonist Ramorelix®. Significant anti-proliferative effects in these tumor cells were observed.

In another embodiment, the above-mentioned cell lines were also treated with a GnRH agonist, including with GOSERELIN® (ZOLADEX®, Buserelin or LEUPRORELIN®) or with a GnRH antagonist such as Antide® or Antarelix®. Significant anti-proliferative effects in these tumor cells were observed.

In another embodiment, the above-mentioned cell lines are also treated with additional GnRH agonists, such as (D-Lys6)-GnRH, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH, (D-Lys6)-Lamprey GnRH II, and Lamprey GnRH III. Significant anti-proliferative effects in these tumor cells were observed.

In another embodiment, the small cell lung carcinoma cell lines NCI-H1688, NCI-H1417, NCI-H1672, NCI-H1836, DMS-79, DM-553, DMS-114, SW-1271, NCI-H2227, NCI-HI1963 and SHP-77 in addition to the multidrug-resistant small cell lung carcinoma cell line H-69 AR, are cultured as described above and then treated as described by Emons, G., et al., 1993, supra, and Irmer, G., 1995, supra, with various concentrations of the GnRH agonists (D-Lys6)-GnRH, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH, (D-Lys6)-Lamprey GnRH II and Lamprey GnRH III. Significant anti-proliferative effects in these tumor cells were observed.

In another embodiment, the above-mentioned cell lines are treated as described by Emons, G., et al., 1993, supra, and Irmer, G., 1995, supra, with a concentration of the GnRH peptide antagonist Ac-D-Nal(2)-D-4-ClPhe-D-Pal-Ser-1-MePal-D-IsopropylLys-Leu-IsopropylLys-Pro-D-AlaNH$_2$ (also known as Ant 135-25; the Mepal portion is known as 1-Methyl-3-[3'-pyridyl]-alanine), Teverelix (also known as Antarelix®), Cetrorelix (also known as Cetrotide®), Abarelix (also known as Plenaxis®), D-63153 (also known as Ozarelix®), acyline, azaline B, antide (also known as Iturelix®), Degarelix (FE200486), Ganirelix, Nal-Glu, Orntide (also known as Ornirelix®), Elagolix, or with antagonist peptidomimetic ((2S)-2-[5-[2-(2-azabicyclo[2,2,2]oct-2-yl)-1,1-dimethyl-2-oxoethyl]-2-(3,5-dimethylphenyl)-1H-indol-3-yl]-N-(2-pyridin-4-ylethyl-)propan-1-amine (also known as "IN3"). Significant anti-proliferative effects in these tumor cells were observed.

In another embodiment, the small cell lung carcinoma cell lines NCI-H1688, NCI-H1417, NCI-H1672, NCI-H1836, DMS-79, DM-553, DMS-114, SW-1271, NCI-H2227, NCI-HI1963 and SHP-77 in addition to the multidrug-resistant small cell lung carcinoma cell line H-69 AR, are cultured as described above for the above-mentioned cell lines, and then treated as described by Emons, G., et al., 1993, supra, and Irmer, G., 1995, supra, with a concentration of the GnRH antagonist Cetrorelix (also known as Cetrotide®) or with a GnRH peptide antagonist Ac-D-Nal(2)-D-4-ClPhe-D-Pal-Ser-1-MePal-D-IsopropylLys-Leu-IsopropylLys-Pro-D-AlaNH$_2$ wherein Mepal is 1-Methyl-3-[3'-pyridyl]-alanine or Ant 135-25 (also known as Ac-D-Nal(2)-D-4-Cl-Phe-D-Pal-Ser-1-MePal-D-IsopropylLys-Leu-IsopropylLys-Pro-D-AlaNH$_2$), Teverelix (also known as Antarelix®), Cetrorelix (also known as Cetrotide®), Abarelix (also known as Plenaxis®), D-63153 (also known as Ozarelix®), acyline, azaline B, antide (also known as Iturelix®), Degarelix (FE200486), Ganirelix, Nal-Glu, Orntide (also known as Ornirelix®) or with antagonist peptidomimetic ((2S)-2-[5-[2-(2-azabicyclo[2,2,2]oct-2-yl)-1,1-dimethyl-2-oxoethyl]-2-(3,5-dimethylphenyl)-1H-indol-3-yl]-N-(2-pyridin-4-ylethyl-)propan-1-amine (also known as "IN3"). Significant anti-proliferative effects in these tumor cells were observed following application of the above compounds to the described cell types.

In another embodiment, the cell lines used above were each additionally treated with a second GnRH antagonist, namely one of the GnRH antagonists Cetrorelix®, Ant 135-25, IN3, degarelix, Antarelix®, Antide®, and Ramorelix® or alternatively with one of the GnRH antagonists that have been disclosed in U.S. Pat. Nos. 6,939,88, 6,200,957, 5,296,468, 4,851,385, 7,361,633, 7,288,517, WO/2009/106597 or PCT/EP2009/052326, U.S. Pat. Nos. 5,480,969, 5,198,533, or UK Patent GB 2 246782 B, wherein these additional treatment procedures were carried out in a manner similar to those reported in Emons et al., supra, using SB 75 (Cetrorelix®). Presently, a significantly stronger anti-proliferative effect than previously reported using Cetrorelix® only (see Emons et al., supra), was shown to occur.

The cell lines referred to above were also treated separately with monoclonal antibodies against a GnRH receptor antigen described by Karande, A. A., et al., 1995, Mol. Cell. Endocrinol. 114 (1-2), p. 51-56. Presently, significant anti-proliferative effects were observed for these specific cell lines, similar to an anti-proliferation effect observed for another cell line, OVCAR-3 (Ackermann, R. C., et al., 1994, Cancer Letters, 81, 177-184).

Example 4

In vivo Study in the Model of Xenotransplantation

An In vivo Study with Nude Mice

An effect of the treatment of tumor-implanted nude mice (Pinski et al., supra) each with one of the GnRH agonists Buserelin, Triptorelin, Goserelin, and Leuprorelin and each with one of the GnRH antagonists Cetrorelix® (SB-75), Antarelix®, Antide®, and Ramorelix® on the growth of malignant gliomas U-87MG and U-373MG was carried out using daily dosages and controls in nude mice using analysis techniques described for the determination of the efficacy of similar peptides in Pinski et al., supra. Significant growth-inhibiting effects could be observed in these tumors following treatment with the GnRH agonists and GnRH antagonists described in the instant invention.

Example 5

Phase I Study

Patients with non-resectable Glioblastoma multiforme following microsurgical resection and/or after external conventional radiotherapy and/or brachytherapy; or patients with a diffusely, intraaxially growing brain tumor, multifocal tumor spreading or presence of a gliomatosis cerebri, respectively; a tumor volume of more than 65 ml; or a minimal tumor diameter of more than 5 cm, were each treated with the GnRH agonist Buserelin, which was administered intravenously or alternatively by intranasal application as a permanent medication as described by Klijn, J. G. M., et al., 1982, The Lancet, May 19, 12143-1214. Following GnRH agonist treatment, a reduction in tumor volume is clearly observed on MRT or CT images, respectively. A recidivation-free survival (i.e. no recurrence of the tumor) longer than that described following Tamoxifen treatment of glioma (Pollack et al., 1995, Pediatr. Neurosurgery 22, 281-288) was observed.

Example 6

Phase I Study

Patients with inoperable, stereotactically confirmed Glioblastoma multiforme (after conventional radiotherapy) were treated under permanent medication with ZOLADEX® in the dosage and administration form as cited for metastasizing mammary carcinoma in the ROTE LISTE®. MRT controls reveal a significant reduction in tumor volume.

Example 7

Phase II Study

Patients with histologically confirmed Glioblastoma multiforme following a first operation were treated (also randomized controlled) with ZOLADEX® in the manner described by Jonat et al., 1995, European J. Cancer, 137-142. Following radiotherapy, the patients are assigned to two different groups. One group received treatment, for example with ZOLADEX® and one group without ZOLADEX® (or with Cetrorelix® and without Cetrorelix®, or with ANTIDE® and without ANTIDE®, or with DECAPEPTYL® or without DECAPEPTYL® etc.). The resulting clinical effects are similar to metastasized perimenopausal mammary carcinoma. The percentage of patients showing an actual significant therapy effect is evaluated according to the criteria of tumor volume, recidivation-free survival, overall survival following initial application of the compound, and Karnofsky and Spitzer indices in a clinical neurological examination and under consideration of the other examination criteria (Sposto, R., et al., 1989, J. Neurooncology, 7, 165-177, and Kirby, S., et al., 1995, J. Natl. Cancer Institute, 87, 1884-1888, 1995). Resulting MRT and/or CAT scans revealed a significantly higher reduction in tumor volume or significantly longer recidivation-free survival and significantly longer overall survival following initial application, respectively, than in the control group not treated with ZOLADEX®.

Through the use of conventional gene therapy methods that are well-known to the skilled person, retroviruses and antisense GnRH receptor vectors are stably transfected into glioma cells, and a resulting anti-proliferative effect is observed.

Example 8

Collection of Glioma Tissue

During brain tumor operations (peroperatively), fresh human tumor tissue was collected dry in a small, sterile dish without the addition of medium and immediately transferred into a sterile standard plastic tube. The tube was sealed airtight and after about 15 minutes shock-frozen in a Dewar container (Union Carbide Cryogenic Equipment 35HC, ref. No. 103-139-T5) containing liquid nitrogen. The tissue samples were stored in liquid nitrogen for about 2 months until GnRH receptor determination.

Example 9

Tissue Preparation

The frozen tissue samples collected above were rinsed to eliminate residual blood and fat and then cut into pieces of about 2×2×2 mm using a scalpel. The tissue samples were homogenized for 1 minute at maximum output in a Dismembrator II (B. Braun, Melsungen). The homogenized tissue was resuspended in 1000 µl of cold buffer 1 (10 mM tris-(hydroxymethyl)-aminomethane, pH 7.4, 4° C.) and mixed until a homogenous mixture was achieved. In a first centrifugation step (800×g, 10 minutes, 4° C.), the sample was separated from larger tissue debris. The supernatant was again centrifuged (10.000×g, 45 minutes, 4° C.). The supernatant of the second centrifugation step was discarded, and the pellet containing the membrane fraction was resuspended in 1000 µl of cold buffer 1 and homogenized using a Polytron homogenizer three times for 4 seconds each to obtain an as homogenous membrane suspension as possible. To this membrane fraction, 1000 µl of cold buffer 1 were added. This suspension was used for determining the concentration of GnRH receptors using the radio receptor assay as described above.

Example 10

Determination of the Protein Concentration

The BioRad reagent was diluted 1:5 with distilled water. 3.5 ml of this reagent were mixed with 50 µl of the prepared membrane fraction and incubated for 5 minutes. Photometric measurement of the protein concentration was carried out as a double determination at a lambda of 595 nm using conventional methods. A human albumin protein standard which is correspondingly used for the measurement serves as the protein standard.

Example 11

Radio Receptor Assay

The determination GnRH receptor concentration was carried out in the membrane fraction of the prepared tissue as described above. The radio receptor assay comprised two different samples, each of which is determined in four replicates: a) samples containing the prepared membrane fraction, and b) control samples.

a) 300 µl buffer 2 (10 mM tris-(hydroxymethyl)-aminomethane, pH 7.4, 0.1% bovine serum albumin) and 100 µl of tracer ($^{125}$I-Buserelin, 80,000 cpm/100 µl) was added to 100 µl of membrane fraction.

b) For the controls, 250 µl buffer 2, 100 µl of tracer, 100 µl of membrane fraction and 50 µl GnRH analogue ($10^{-5}$ M Buserelin) are mixed.

Each individual sample was well-mixed and then incubated for 90 minutes at 4° C. The radio receptor assay was stopped by addition of 500 µl of bovine gamma globulin solution (0.1% bovine gamma globulin, 0.15 M NaCl). Subsequently, 1000 µl of a 25% PEG-6000, 0.15 M NaCl solution were added.

The samples were again mixed until homogenous and incubated for 20 min at 4° C. Separation of the PEG-hormone receptor complexes was performed via a centrifugation step (1.600×g, 30 minutes, 4° C.) during which the complexes due to their higher mass form the pellet. The supernatant is removed carefully using a Pasteur pipette. The number of counts per minute formed the basis for evaluating the GnRH receptor content as determined in a Gamma counter (Berthold).

Example 12

Results and Analysis of the Radio Receptor Assay

Generally, several tissue samples were used in an experimental approach. To exclude a systematic error in the case of a negative result of all samples in one assay, a standard sample from bovine pituitary tissue was examined in each of the assays in parallel to the tumor tissues. Thus, the detection of GnRH receptors in bovine pituitary tissues served as a positive control. The pituitary tissue was prepared similar to the tumor tissues and the membrane fraction was also purified in a like manner.

Example 13

Evaluation of the GnRH Receptor Content

The evaluation of the GnRH receptor content (fmol/mg of membrane protein) was carried out on the basis of the counts per minute (cpm), the specific binding, the amount of protein used, and the specific activity of the radiolabeled ligand.

The specific binding ($B_{spec}$) is calculated from the difference of the mean value of the four-fold determination of total binding ($B_O$) and the mean value of the four-fold determination of unspecific binding (NSB).

The amount of protein used is determined photometrically as described above.

Experimental Data: Analogue $^{125}$I-Buserelin:
MG: 1253 g/mole
Specific Activity: 1470 mCi/mg
Activity of $^{125}$I-Buserelin solution 20 µCi/ml
  1470 mCi/mg $^{125}$I-Buserelin=54.4×$10^9$ Bq/mg
  1 ml of $^{125}$I-Buserelin solution includes: 13.61×$10^{-9}$ g $^{125}$I-Buserelin with 7.4×$10^6$ Bq
  13.61×$10^{-9}$ g/ml $^{125}$I-Buserelin=10.9×$10^{-12}$ mole $^{125}$I-Buserelin, 54.4×$10^9$ Bq=44.4×$10^7$ cpm
  10.90×$10^{-12}$ mole $^{125}$I-Buserelin=44.4×$10^7$ cpm
  1000 cpm correspond to 0.247×$10^{-15}$ mole $^{125}$I-Buserelin.

For the calculation of the GnRH receptor concentration (fmol/mg of membrane protein) from the cpm values measured, the amount of protein used and the disintegration factor must also be considered. Thus, the equation for the calculation of the GnRH receptor content is the following:

$$\frac{0.247 \times 10^{-15} \text{ mole } ^{125}\text{I-Buserelin}}{\text{disintegration factor} \times \text{amount of protein}} = 1000 \text{ cpm}$$

TABLE II

Determination of GnRH receptor concentration

| | ER fmol/mg prot | PgR fmol/mg prot | GnRH receptor atomol/mg prot | FINDING |
|---|---|---|---|---|
| | 10 | 20 | 1000 | Negative |
| | 10-20 | 20-30 | 1000-3000 | weakly positive |
| | 20 | 30 | 3000-5000 | Positive |
| | 50 | 100 | 5000 | strongly positive |
| Histological samples | | | | |
| Chordoma | 1 | 1 | 708 | |
| GBM | 1 | 2 | 2478 | |
| GBM | 1 | 1 | 895 | |
| GBM | 1 | 1 | 1111 | |
| G II Glioma | 1 | 1 | 3635 | |
| Meningeoma | 1 | 74 | 1 | |
| Adenocarcinoma | 1 | 1 | 1 | |
| GBM | 1 | 1 | 7357 | |
| Fibrillary G II Astrocytoma | 1 | 1 | 1 | |
| Meningeoma | 1 | 177 | 7444 | |
| Meningeoma | 1 | 550 | 1588 | |
| GBM | 1 | 1 | 4466 | |
| Additional values: | | | | |
| Chordoma | 1 | 1 | 1117 | weakly positive |
| Intraspinal meningeoma | 3 | 7 | 1640 | weakly positive |
| Brain metastasis of plate epithelium carcinoma of the lung | 1 | 1 | 200 | negative |
| Normal brain tissue | 4 | 1 | 460 | Negative |

According to the invention, results of the GnRH receptor determination using the radio receptor assay of tissue samples of several patients are listed:
ABBREVIATIONS: ER: Estrogen receptor; PgR: Progesterone receptor

Example 14

Proliferation Assay Using the Human Malignant Melanoma Cell Line MV3

The human melanoma cell line MV3 was cultured (in long-term culture in RPMI medium (Gibco Co.) with 1% Penstrep and 10% of heat-inactivated fetal calf serum). The proliferation assay was carried out with $6 \times 10^2$ cells per well in 96 well plates. First, the cells were removed from the culture flask with a 0.02 mM solution and then washed in standard PBS solution. Following centrifugation for 10 minutes (1200 g) the supernatant was discarded and the pellet resuspended in 1 ml medium. An aliquot of 20 µl of the cells was diluted with trypan blue to obtain an 1:20 dilution. Trypan blue stains the necrotic cells. Then counting was performed in a Neubauer counting chamber. Evaluation was performed by daily determination of 4 values starting at day 0 and multiplying the mean values of the cell counts$\times 10^4 \times$ dilution factor 20 to obtain the cell count. During the 5 days, the measurement was performed 4× daily in a Biomec spectrophotometer.

The method for determination of tumor cell proliferation is described in Lü, H. Q., et al., 1996, Journal of Cancer Research and Clinical Oncology, 122, 335-342.

The cell line was treated with (Gly-OH10)-LHRH, the LHRH hormone (FIG. 3) (Sigma Chemical Co., No. L8008) or Triptorelin, an LHRH agonist (FIG. 2) (Sigma Chemical Co., No. L9761) or Antide®, a LHRH antagonist (FIG. 1) (Sigma Chemical Co., No. A8802).

Using concentrations of $10^{-4}$ M, $10^{-5}$ M, and $10^{-6}$ M, with the medium serving as a negative control from day 4 on, the following results were obtained:

Referring to FIG. 1: For Antide® (a GnRH antagonist), a clear inhibition of proliferation is observed with high concentrations of $10^{-4}$ M and $10^{-5}$ M of 15% and 35%, respectively, (see Emons et al., 1993, supra, but present results presented a later onset as compared to the ovarian carcinoma cell lines used by Emons, where an anti-proliferative effect of the antagonists in one of the two cell lines occurred from day 1 on). At a concentration of $10^{-6}$ M, no inhibition of the proliferation was observed; rather, a stimulation of the growth of 40% resulted. This paradox in vitro effect of GnRH antagonists is similar to GnRH-bearing prostate carcinomas described by Limonta et al., 1993, J. Clin. Endocrinol. Metab., 76, 839-845. A similar in vitro effect for relatively low concentrations is also well-known for Tamoxifen in the MCF-7 mammary carcinoma cell line (Zänker, K., et al., 1995).

For Triptorelin® (a GnRH agonist) (see FIG. 2) a 15% inhibition of the tumor cell proliferation was observed from day 4 on at the concentrations mentioned. In Emons et al., 1993, supra, this has been observed already starting from day 1 for both ovarian carcinoma cell lines under a Triptorelin® treatment of $10^{-5}$ M, and 40% inhibition was observed on day 6.

The above findings show the presence of a direct antiproliferative effect of Antide® and Triptorelin® on malignant melanoma cells. The above findings additional show that GnRH receptors are in fact present on the human malignant melanoma cell line MV 3, since binding of a non-ligand to the tumor cells can be excluded.

Figure 2:
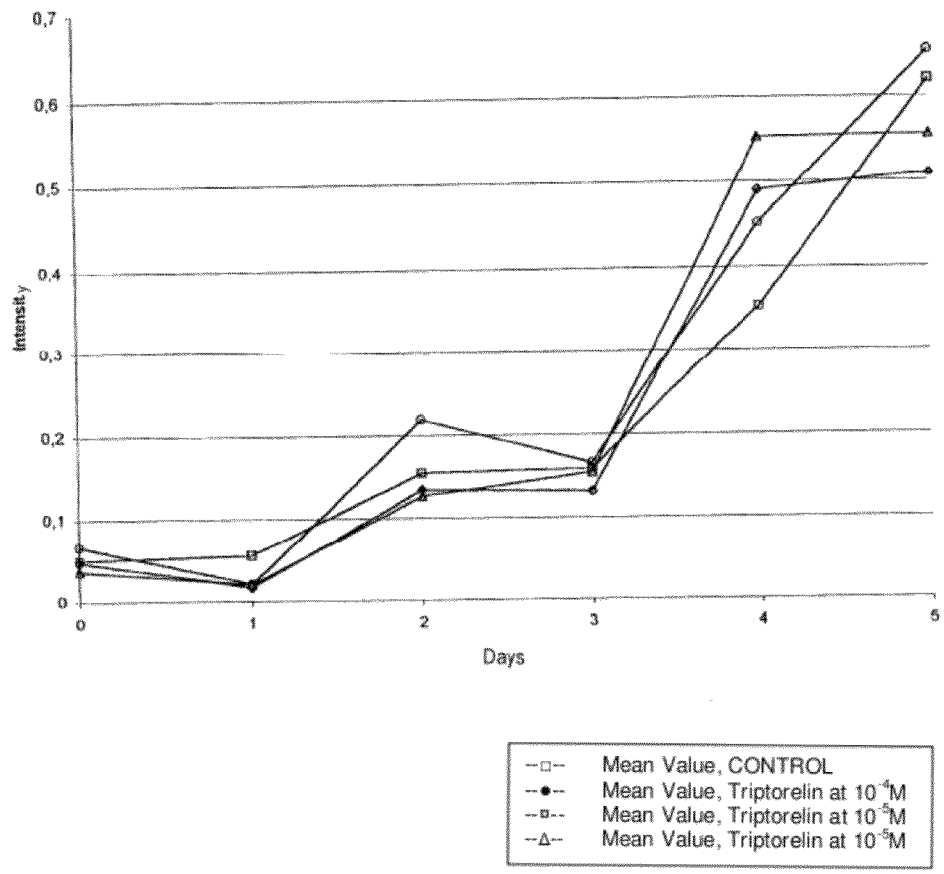
FIG. 2: Inhibition of proliferation on malignant melanoma MV3 cells by Triptorelin® (GnRH agonist).
Figure 3:
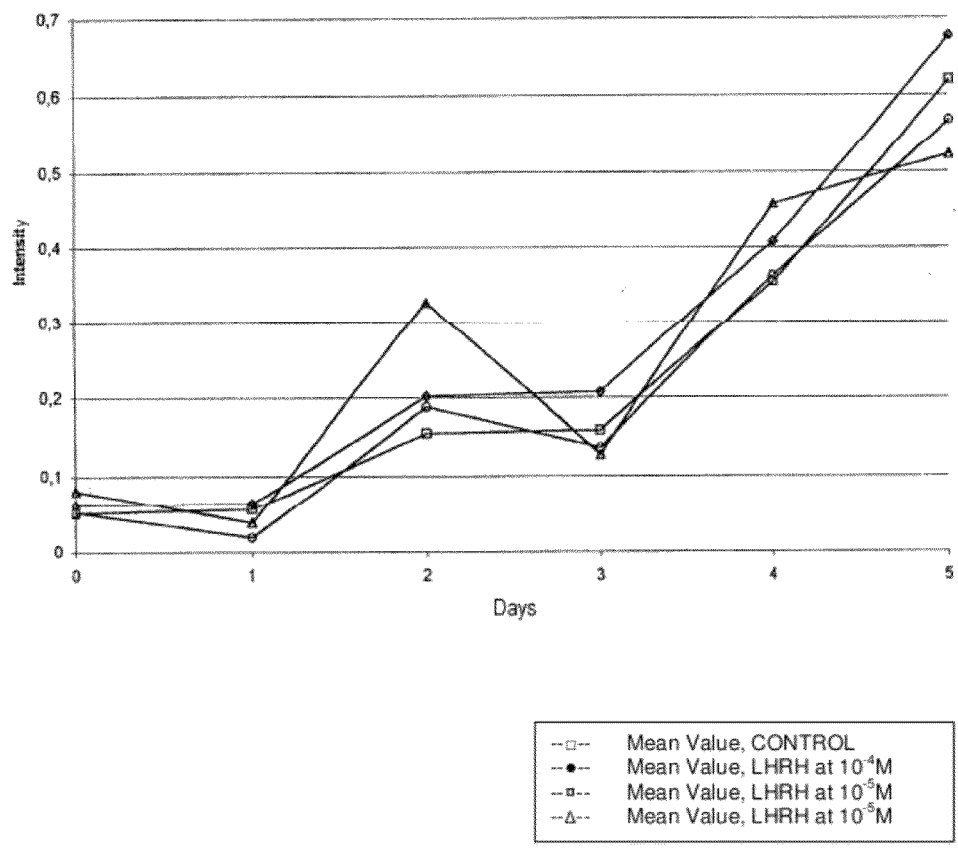
FIG. 3: Inhibition of proliferation on malignant melanoma MV3 cells by LHRH hormone.

The graphs depicted in FIGS. 1-3 conclusively show that malignant melanoma MV3 is a LHRH hormone-dependent tumor.

Thus, also in vitro the LHRH hormone functions as a positive growth factor. The function of LHRH hormone produced in an autocrine manner is inhibited by both Antide® and Triptorelin®.

Example 15

GnRH Agonist as an Inhibitor of Cell Proliferation and Invasive Growth of Melanoma Cells In another embodiment, as demonstrated by RT-PCR and by Western blot analysis, GnRH receptors are shown to be expressed in the highly proliferative and metastatic BLM melanoma cell line. Disclosed is a dose-dependent inhibition of cell proliferation after the treatment of BLM cells with a GnRH agonist. In addition, the activation of the GnRH receptors also reduces the ability of melanoma cells to invade a reconstituted basement membrane.

Cell Proliferation Studies

BLM cells were plated at a density of 700 cells/cm$^2$ in 10-mm dishes in culture medium. Cells were allowed to attach and start growing for 3 days; the seeding media were then changed. Cells were treated daily (the drug was added to the medium every day), for 7 days, with LHRH-A ($10^{-11}$-$10^{-6}$ M); the medium was changed at every two days. At the end of the treatment, cells were collected and counted by hemocytometer.

To confirm the specificity of the action of LHRH-A on melanoma cell proliferation, it was investigated whether the effects of the LHRH agonist might be counteracted by a potent GnRH antagonist. A preliminary experiment was performed to select the dose of the GnRH antagonist (ANT) to be used. To this purpose, BLM cells were treated daily with ANT at different doses ($10^{-11}$-$10^{-6}$ M).) Cells were harvested and counted after 7 days of treatment. Subsequently, BLM cells were treated daily, for 7 days, with LHRH-A ($10^{-7}$ M), either in the absence or in the presence of ANT ($10^{-7}$ M). Cells were counted 7 days after the beginning of the treatment.

The antiproliferative action of GnRH agonists on melanoma cells is further investigated in another melanoma cell line (Me15392). These experiments have been carried out as described above for BLM cells (same GnRH agonist, same doses of the drug and same length of treatment, etc.).

All proliferation experiments were performed in four to six replicates. The data obtained from three independent experiments were analyzed according to the Dunnett's test after one-way ANOVA.

Matrigel Gel Assay

For invasion and migration experiments, the $10^{-6}$ M dose of LHRH-A has been chosen, since it was the most effective in earlier proliferation studies. This dose has been also used in previous papers analyzing the interaction between GnRH agonists and stimulatory growth factors in prostate cancer cells.

Subconfluent BLM cells were collected by trypsinization, resuspended in culture medium and seeded in 20 µL (150,000 cells/drop) on the lid of a culture dish. The lid was then placed on a dish filled with 2 mL of culture medium and incubated at 37° C. for 48 h. Matrigel solution (80 µL, 2.7 mg/mL) was pipetted onto the bottom of wells of a 24-well culture dish, and left to set at 37° C. Cell aggregates were transferred over the cushion and then overlaid with additional 20 µL of Matrigel. The aggregates into Matrigel were covered with 400 µL culture medium in the absence or in the presence of LHRH-A ($10^{-6}$ M). The aggregates were then observed daily under a light microscope and at the end of the incubation time phase-contrast pictures of the aggregates were taken.

Chemomigration Assay

The assay was performed using a 48-well Boyden's chamber, according to the manufacturer's instruction (Neuroprobe, Cabin John, Md.). Subconfluent BLM cells, grown in culture medium, were pretreated for 5 days with LHRH-A ($10^{-6}$ M) and harvested at the end of the treatment. BLM cell suspensions ($10^5$ cells/50 µL), resuspended in culture medium deprived of FBS, were placed in the open-bottom wells of the upper compartment of the chamber. Each pair of wells were separated by polyvinylpyrrolidone-free polycarbonate porous membrane (8-µm pores) pre-coated with gelatin (0.2 mg/mL in PBS). The chemoattractant (FBS 5%) was placed in the lower compartment of the chamber. The chamber was then kept for 4 h in the cell culture incubator. After that, the cells migrated through the pores, and adhered to the underside of the membrane, were fixed, stained (Diff-Quick kit, DADE, Dudingen, CH) and mounted onto glass slides. For quantitative analysis, six random objective fields of stained cells were counted for each well (8 wells/experimental group) and the mean number of migrating cells/mm$^2$ was calculated. The data obtained from four independent experiments were compared by ANOVA and Dunnett's test.

Results

Expression of GnRH and of the GnRH Receptor in BLM Melanoma Cells

Figure 4:
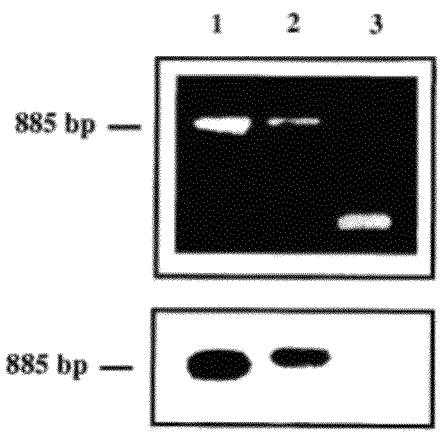
FIG. 4: RT-PCR analysis of the expression of GnRH in BLM (human melanoma) cells. Top: Ethidium bromide-stained agarose gel of the amplified cDNAs. Bottom: Autoradiography of the Southern blot obtained from the gel shown in the top panel after hybridization with a $^{32}$P-labeled oligonucleotide GnRH cDNA probe. lane 1: BLM cells; lane 2: prostate cancer cells; lane 3: TR-PCR, control (308 bp). One experiment representative of three is reported.

The expression of GnRH and of GnRH receptor mRNA in melanoma BLM cells was investigated by RT-PCR. After PCR, the amplified cDNAs were electrophoresed on a 1.5% agarose gel containing ethidium bromide. With regard to the expression of GnRH, the predicted 228-bp fragment is observed in BLM cells (FIG. 4, upper panel, lane 1) as well as in prostate cancer cells used as controls (FIG. 4, upper panel, lane 2). No cDNA band is detected in samples without RT (data not shown), ruling out the possibility of genomic DNA contamination. After Southern blotting, the cDNA fragments obtained from BLM and prostate cancer cells, hybridizes with the $^{32}$P-labeled oligonucleotide probe specific for GnRH cDNA (FIG. 4, lower panel, lanes 1 and 2).

Figure 5:
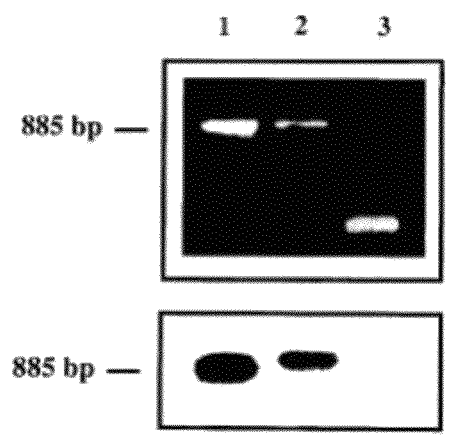
FIG. 5: RT-PCR analysis of the expression of GnRH receptor in BLM cells. Top: Ethidium bromide-stained agarose gel of the amplified cDNAs. Bottom: Autoradiography of the Southern blot obtained from the gel shown in the top panel after hybridization with a $^{32}$P-labeled oligonucleotide GnRH receptor cDNA probe. lane 1: BLM cells; lane 2: prostate cancer cells; lane 3: TR-PCR control (308 bp). One experiment representative of three is reported.

In the case of the expression of the GnRH receptor mRNA, the results obtained demonstrate that the predicted 885-bp cDNA fragment can be obtained in BLM (FIG. 5, upper panel, lane 1), as well as in prostate cancer cells (FIG. 5, upper panel, lane 2). No cDNA band is amplified in samples without RT (data not shown). As expected, the GnRH receptor cDNA bands hybridize with the specific $^{32}$P-labeled oligonucleotide probe specific for GnRH receptor cDNA (FIG. 5, lower panel, lanes 1 and 2).

Figure 6:
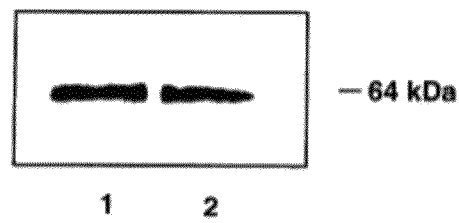
FIG. 6: Western blot analysis of solubilized membrane proteins from BLM cells (lane 1) and prostate cancer cells (lane 2), probed with the monoclonal antibody from FIG. 4 raised against the human pituitary GnRH receptor. One experiment representative of three is reported.

The presence of GnRH receptors in melanoma cells has been further investigated at the protein level, by Western blotting technique, and by using the FIG. 4 monoclonal antibody specifically raised against the human pituitary GnRH receptor. As shown in FIG. 6, a major protein band of approximately 64 kDa molecular mass is identified by the antibody in BLM cells (lane 1) like in prostate cancer cells (FIG. 6, lane 2). This molecular weight corresponds to that previously reported for the human pituitary GnRH receptor. The level of expression of this receptor is not found to be affected by a 7-day treatment with the GnRH agonist (data not shown).

Effect of GnRH Agonists on the Proliferation of BLM Melanoma Cells

Figure 7:
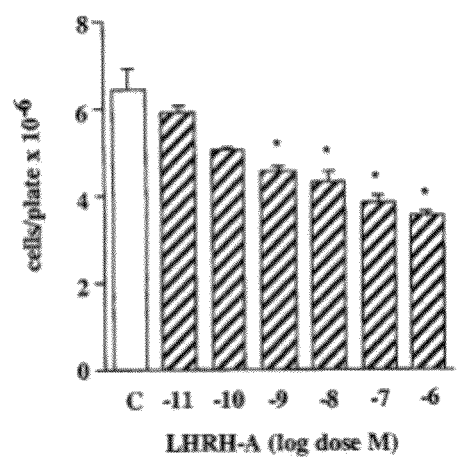
FIG. 7: Effects of the GnRH agonist (LHRH-A) on the proliferation of BLM cells. Results are expressed as mean cell number per plate±SE. *, $p<0.05$ vs. control (C).

The observation that both GnRH and GnRH receptors are expressed in BLM cells, prompted us to investigate whether this GnRH-based system might be involved in the local control of melanoma cell growth. To this purpose, BLM cells were treated daily, for 7 days, with the potent GnRH agonist LHRH-A ($10^{-11}$-$10^{-6}$ M). The treatment resulted in a significant and dose-dependent inhibition of cell proliferation (FIG. 7).

Figure 8A:
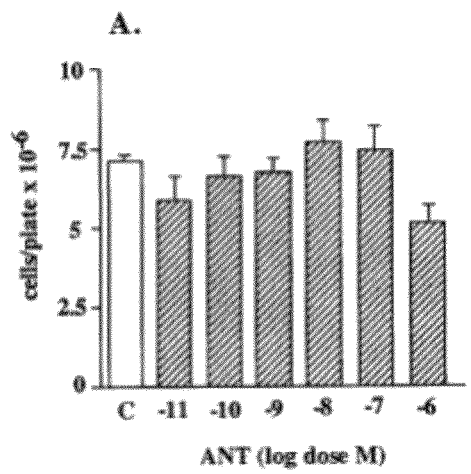
FIG. 8: A) Effect of the GnRH antagonist (ANT) on the proliferation of BLM cells. B) Effect of the GnRH antagonist (ANT, $10^{-7}$M) on the inhibition of BLM cell proliferation induced by the GnRH agonist (LHRH-A, $10^{-7}$M). Results are expressed as mean cell number per plate±SE. *, $p<0.05$ vs. control (C).
Figure 8B:
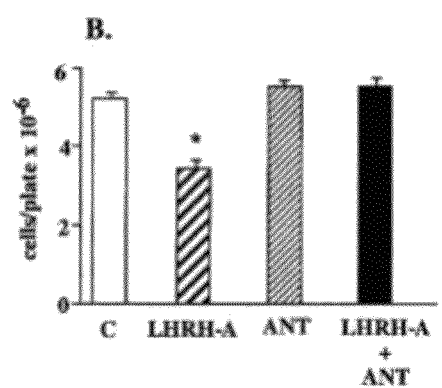

Further studies were performed to evaluate whether the antiproliferative action of LHRH-A on melanoma cells could be antagonized by the simultaneous treatment of the cells with the GnRH antagonist ANT. In preliminary experiments, the activity of ANT was evaluated. FIG. 8A shows that the antagonist does not affect the proliferation of the cells, when given at the doses $10^{-11}$-$10^{-7}$ M. The compound reduces slightly, but not significantly, the growth of BLM cells at the dose of $10^{-6}$ M. For subsequent experiments, the dose of $10^{-7}$ M was then selected. FIG. 8B confirms that ANT ($10^{-7}$ M), when given alone, has no effect on cell proliferation; on the other hand, ANT totally blocks the antiproliferative action exhibited by LHRH-A.

Expression and Role of GnRH Receptors in Me15392 Melanoma Cells

Figure 9:
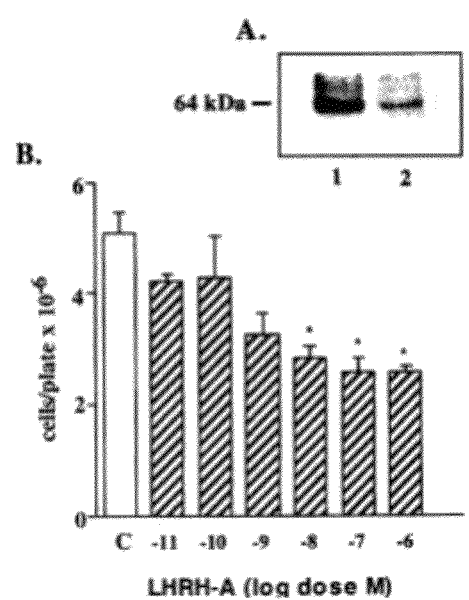
FIG. 9: A) Western blot analysis of the expression of the GnRH receptor in Me15392 (human melanoma) cells. lane 1: BLM cells; lane 2: ME15392 cells. B) Effect of the GnRH agonist (LHRH-A) on the proliferation of Me 15392 cells. Results are expressed as mean cell number per plate±SE. *, $p<0.05$ vs. control (C).

The presence of GnRH receptors, and their role in the control of melanoma cell proliferation have been further investigated in an additional melanoma cell line (Me15392). By Western blot analysis, and by using the FIG. 4 monoclonal antibody, we demonstrate that a protein band of 64 kDa is present in membrane preparations from Me15392 cells (FIG. 9A, lane 2). The molecular weight of this band corresponds to that found in BLM cells (FIG. 9A, lane 1).

Like in the case of BLM cells, the treatment of Me15392 cells with LHRH-A ($10^{-11}$-$10^{-6}$ M), for 7 days, results in a significant and dose-dependent inhibition of cell proliferation (FIG. 9B).

Binding Parameters of LHRH Receptors in BLM and Me15392 Melanoma Cells

GnRH receptors in melanoma cells have been analyzed also in terms of binding parameters. Binding sites for $^{125}$I-LHRH-A have been found to be present on the membranes of both BLM and Me15392 cells. Computer analysis of the data obtained from the displacement curves revealed the presence of a single class of high-affinity binding sites ($K_d$ in the nanomolar range) in both melanoma cell lines, as well as in rat pituitaries used as controls (Table III).

TABLE III

Characteristics of $^{125}$I-LHRH-A binding to human melanoma cell membranes

| | Dissociation constant | $^{125}$I-LHRH-A binding Capacity (fmoles/mg protein) |
|---|---|---|
| BLM cells | 0.7-1.1 nM | 150-200 |
| ME15392 cells | 0.1-0.6 nM | 200-250 |
| Rat pituitaries | 1.5-2.0 nM | 70-100 |

Binding characteristics were evaluated from displacement curves as described in Materials and Methods.

This observation agrees with previous data showing the expression of high-affinity GnRH receptors in tumors of the reproductive tract.

Effect of GnRH Agonists on the Metastatic Potential of BLM Melanoma Cells

Figure 10:
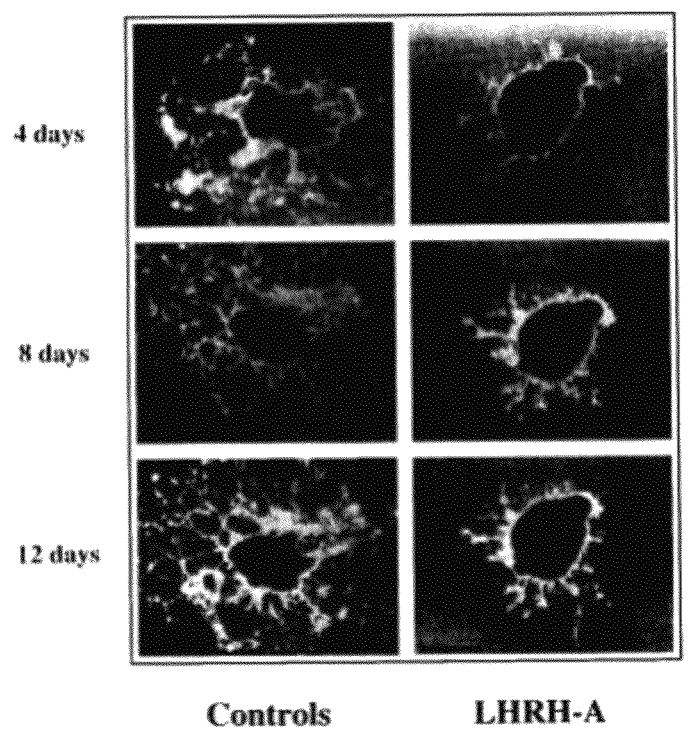
FIG. 10: Effects of the GnRH agonist (LHRH-A) on the capacity of BLM melanoma cells to invade a reconstituted basement membrane after 4, 8, and 12 days of treatment. Results from one experiment representative of four are reported. Scale bar: 700 µm.

These experiments have been performed to verify whether the activation of locally expressed GnRH receptors might affect the metastatic potential of melanoma cells. First, we have studied the effects of the GnRH agonist LHRH-A ($10^{-6}$ M) on the ability of BLM cells to invade a matrix of a reconstituted basement membrane (Matrigel). BLM cells spontaneously form cell aggregates in Matrigel, when prepared by the hanging-drop technique. FIG. 10 shows that BLM cells actively leave the aggregate, and invade the Matrigel preparation at 4, 8 and 12 days. The treatment of BLM cells with ZOLADEX® completely abrogates the migration of the cells through the Matrigel, at all time intervals considered (FIG. 10).

Figure 11:
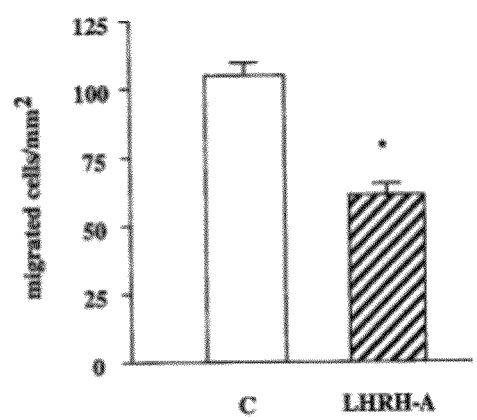
FIG. 11: Effects of the GnRH agonist (LHRH-A) on the ability of BLM melanoma cells to migrate toward a chemotactic stimulus (FBS 5%). $p<0.05$ vs. control (C).

We then examined whether GnRH agonists might affect the ability of melanoma cells to migrate towards a chemoattractant, using the Boyden's chamber technique and FBS 5% as the chemotactic stimulus. We have observed that when BLM cells were pretreated with ZOLADEX® ($10^{-6}$ M) for 5 days, the number of the cells that migrate in response to the chemo attractant is significantly decreased when compared to control cells (FIG. 11).

Example 16

GnRH Agonist as an Inhibitor of Tumor Cell Proliferation

In vivo study in nude mice inoculated with malignant melanoma.
Low Dosage Experiment:
Materials and Methods
Sixteen male nude mice were injected s.c. in the flank with $1\times10^6$ (0.2 ml/mouse) BLM cells. The treatment started the same day: Eight mice received daily 100 µg ZOLADEX® per mouse in 200 µl saline. Eight control mice were treated with 200 µl saline each. The treatment lasted 2-3 weeks. Every 2 to 3 days the volume of the tumors was determined by caliper.
Results
BLM cells, when injected i.v. give rise to metastases, mainly in the heart. The BLM tumors grew faster in the controls. In ZOLADEX®treated mice, measured tumors were 15-20% smaller with respect to the controls.
The low-dosage results are comparable with standard melanoma chemotherapy (10%)(dacarbazine), showing that GnRH agonist can inhibit tumor growth in vivo.

Example 17

GnRH Agonists Inhibits the Growth of Glioblastoma Cells Expressing the GnRH Receptor The presence of GnRH binding sites on glioblastoma cells represents an important diagnostic marker for nervous system tumors. We disclose the expression of GnRH receptors and their possible role in the control of high-grade glioma growth.
Materials and Methods
Chemicals
The GnRH agonist ZOLADEX® [D-Ser(tBu)$^6$Aza-Gly-LHRH] was kindly provided by AstraZeneca Pharmaceuticals, Divisione Farmaceutici (Milano, Italy).
Tumor Specimens
Glioblastoma biopsy specimens were either frozen at $-80°$ C. or fixed with formalin and embedded in paraffin. Brain tissue was examined from a normal section specimen. Histological diagnoses were made according to the most recent WHO classification in 2000 from Kleihues, P. et al. (Kleihues P, Louis, D N, Scheithauer B W, Rorke L B, Reifenberger G, Burger P C, Cavenee W K. The WHO classification of tumors of the nervous system. J Neuropathol Exp Neurol 2002; 61: 215-25).
Cell Cultures
The human glioblastoma U-87 cell line, which is known to have high proliferative activity, was kindly donated by Dr. Gaetano Finocchiaro (Instituto Neurologico Testa', Milano, Italy). Cells were routinely grown in RPMI medium (Seromed, Biochrom K G, Berlin, Germany), supplemented with 10% fetal bovine serum (FBS, Life Technologies, Paisley, Scotland), glutamine (1 mM) and antibiotics (100 UI/ml penicillin G sodium, 100 µg/ml streptomycin sulphate), in a humidified atmosphere of 5% $CO_2$ and 95% air. The human androgen-independent DU145 prostate cancer cell line was used in this study as a positive control, since we have previously shown that a GnRH system is expressed in these cells. (Rambaldi A, Young D C, Griffin J D. Expression of the M-CSF (CSF-1) gene by human monocytes. Blood 1987; 69:1409-1413).
RT-PCR Analysis of GnRH Receptor mRNA
Total RNA from U-87 cells, as well as from DU145 cells and from human pituitary (Clontech, Palo Alto, Calif.) (the latter two cell types serving as positive controls), was prepared according to a modification of the known guanidinium thiocyanate/cesium chloride method (Kakar S S, Grizzle W E, Neill J D. The nucleotide sequences of human GnRH receptors in breast and ovarian tumors are identical with those found in pituitary. Mol Cell Endocrinol 1994; 189:289-295.)
RNA (2 µg) was used in a RT-PCR reaction. cDNA synthesis was performed using the Gene AMP kit (Perkin Elmer Cetus, Norwalk, Conn.) with an oligo(dT)$_{16}$ primer for the reverse transcriptase. Samples containing cDNAs were then amplified in a 100 µl solution containing PCR buffer (50 mM KCl, 10 mM Tris-HCl), 2 mM $MgCl_2$ and 2.5 U Taq polymerase. The amplification was carried out for 35 cycles (1-min denaturation at 94° C., 1-min primer annealing at 50° C., and 2-min primer extension at 72° C.) in the presence of the following primers: 5'-GCTTGAAGCTCTGTC-CTGGGA-3' (SEQ ID NO:1) (sense, −25 to −5, 30 pmol) and 5'-CCTAGGACATAGTAGGG-3' (SEQ ID NO:2) (antisense, 844-860, 30 pmol).[10] We have previously used this pair of primers to amplify GnRH receptor cDNA in prostate cancer cells. (Rambaldi A, Young D C, Griffin J D. Expression of the M-CSF (CSF-1) gene by human monocytes. Blood 1987; 69:1409-1413).
The predicted size of the amplified cDNA fragment was 885 bp. Following the PCR reaction, the amplified cDNA products were separated on a 1.5% agarose gel and then stained with ethidium bromide.
Western Blot Analysis of GnRH Receptor
Membrane fractions from U-87MG and DU145 cells were prepared according to the protocol reported by Limonta et al. (Rambaldi A, Young D C, Griffin J D. Expression of the M-CSF (CSF-1) gene by human monocytes. Blood 1987; 69:1409-1413).
Samples were homogenized in 10 mM Tris-HCl (pH 7.6) buffer containing 1 mM dithiothreitol on ice. For tissue sample homogenization, 50 mg tissue was cut into small pieces and homogenized in 250 µl buffer H (20 mM Tris/HCl (pH 8.0), 150 mM NaCl, 1 mM $CaCl_2$) using a Dounce glass homogenizator. The homogenates were then centrifuged twice for 10 min each at 800×g to remove cellular debris, and the resulting supernatants were additionally centrifuged at 18,000×g to pellet down the membrane fractions. The cell pellets were solubilized in RIPA buffer [50 mM Tris-HCl (pH 7.7), 150 mM NaCl, 0.8% Triton X-100, 0.8% sodium deoxycholate, 0.08% SDS, 10 mM ethylendiamine tetraacetate, 100 µM $Na_3VO_4$, 50 mM NaF, 0.3 mM phenylmethylsulfonylfluoride, and 5 mM iodoacetic acid] and electrophoresed on 10% polyacrylamide gel under reducing conditions. Equal amounts of tissue pellets were solubilized in 10 mM Tris/HCl pH 8.0 containing 0.1% Triton X-100, SDS-PAGE loading buffer was added, and then the samples were electrophoresed on SDS page-10% denaturing polyacrylamide gel under reducing conditions. Proteins were transferred onto a nitrocellulose filter, in 25 mM Tris-HCl (pH 8.3), 92 mM glycine and 20% methanol at 30 V overnight. Filters were probed using the mouse monoclonal antibody raised against the human pituitary GnRH receptor as in FIG. 4 (kindly provided by Dr. A. A. Karande, Dept. of Biochemistry, Indian Institute of Science, Bangalore, India), at a concentration of 5 µg/ml, followed by incubation with an antimouse IgG. Antibody bound to the GnRH receptor was detected with the ECL-Western blotting detection system after a 5 to 10 min exposure to a Hyperfilm-ECL X-ray film (Amersham, Milano, Italy), at room temperature. The specificity of FIG. 4 antibody for the human pituitary GnRH receptor has been previously demonstrated. (Rambaldi A, Young D C, Griffin J D. Expression of the M-CSF (CSF-1) gene by human monocytes. Blood 1987; 69:1409-1413. Dunnett C W. A multiple comparison procedure for comparing several treatments with a control. J Am Stat Assoc 1955; 50:1096-1121.)

Immunohistochemistry

Paraffin embedded, formalin fixed materials were examined for the immunohistochemical expression of GnRH receptor, including 10 glioblastomas, 6 fibrillary astrocytomas, 10 metastatic carcinomas, and various regions of a normal adult human brain. Sections were pretreated using microwaving in 1 mM EDTA buffer, pH 8.0, for 4×5 min. Mouse monoclonal anti-human LHRH receptor antibody, clone BM582 (DPC Biermann, Bad Nauheim, Germany) was used at a concentration of 0.1 µg/ml. Detection was performed with the Chem Mate Link Biotinylated Secondary Antibody system (Dako, Hamburg, Germany) and diaminobenzidine as chromogen using a Tech Mate Horizon automated staining apparatus.

Cell Proliferation Studies

U-87MG cells were plated at a density of 1400 cells/cm$^2$ in 10-mm dishes in standard culture medium. Cells were allowed to attach and start growing for 3 days; the seeding media were then changed to experimental media. Cells were treated for 7 days with ZOLADEX® ($10^{-10}$-$10^{-6}$ M); medium was changed every two days. Following treatment, cells were collected and counted by hemocytometer. Data obtained from three independent experiments were analyzed according to the Dunnett's test after one-way ANOVA.

Results

Figure 12:
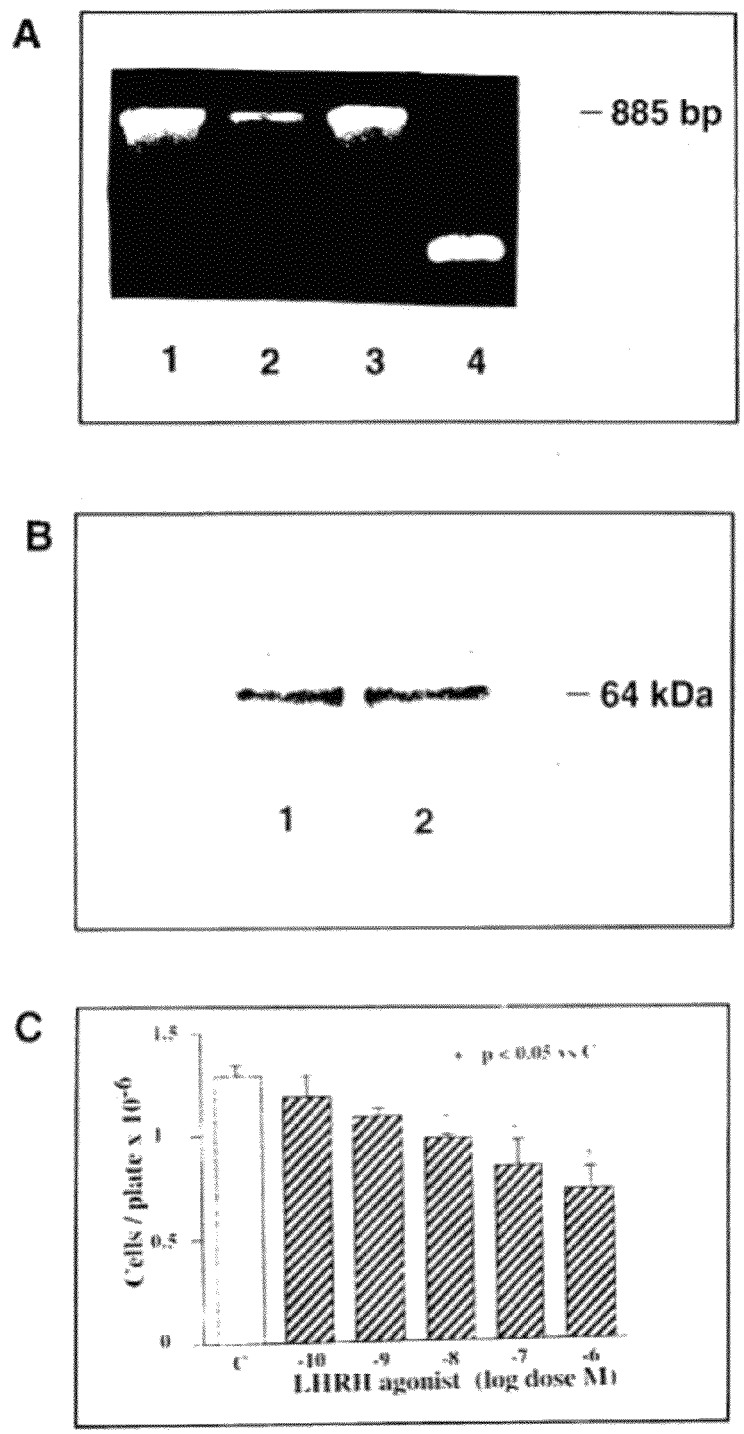
FIG. 12: (A) RT-PCR evaluation of the expression of GnRH receptor mRNA in U-87 glioblastoma cells (lane 1), prostate cancer cells (lane 2), human pituitary (lane 3), and RT-PCR amplification control (lane 4). (B) Western blot analysis of GnRH receptor protein in U-87 glioblastoma cells (lane 1) and prostate cancer cells (lane 2). (C) Effects of GnRH agonist (ZOLADEX®) on U-87 glioblastoma cell proliferation. Data are mean±SE*$p<0.05$ vs. control (C). Results from one experiment representative of three are reported in A and B.

Expression of GnRH Receptors in Cultured Glioblastoma Cells and in Glioblastoma Tissue First, we have verified the expression of GnRH receptor mRNA in U-87MG cells, since specific transcripts were detected by RT-PCR (FIG. 12A, lane 1). The size of the amplified cDNA corresponded to that found in human prostate cancer cells (FIG. 12A, lane 2) and in human pituitary (FIG. 12A, lane 3), (Clontech, Palo Alto, USA) which were used as positive controls. (Rambaldi A, Young D C, Griffin J D. Expression of the M-CSF (CSF-1) gene by human monocytes. Blood 1987; 69:1409-1413).

The presence of GnRH receptors in glioblastoma cells was then confirmed at the protein level. Using standard Western blotting techniques, a band of approximately 64 kDa was identified in U-87MG cell membrane preparations (FIG. 12B, lane 1). A band of the same size was also detected in membrane preparations derived from human prostate cancer cells, which were used as positive controls (FIG. 12B, lane 2). The molecular size of these bands corresponds to that reported for the human pituitary GnRH receptor. (Crawford E D, De Antonio E P, Labrie F, Schroder F H, Geller J. Endocrine therapy of prostatic cancer: optimal form and appropriate timing. J Clin Endocrinol Metab 1995; 80:1062-1078).

Figure 13:
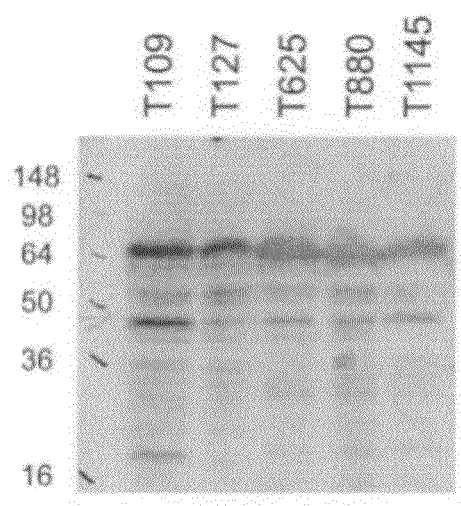
FIG. 13: Western blot of membrane fractions from five glioblastomas, termed T109, T127, T625, T880, and T1145. All five glioblastomas show clearly visible bands at a size of approximately 64 kD.
Figure 14A:
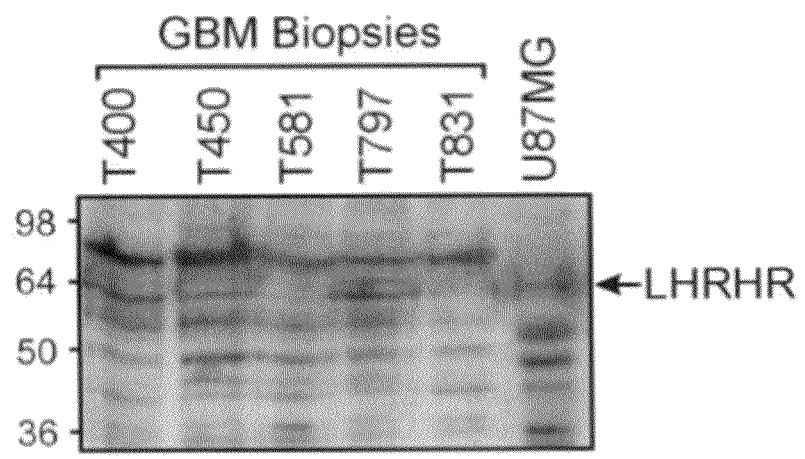
FIG. 14: Western blot of membrane fractions from five glioblastoma biopsies, termed T400, T450, T581, T797, and T831. All five glioblastoma biopsies show clearly visible bands of LHRH receptor at a size of approximately 64 kD. In (A), the U-87 MG glioblastoma cell line was used as a control. In (B), the same five glioblastoma biopsies were subject to a Western blot. The U373MG glioblastoma cell line was used as a control.
Figure 14B:
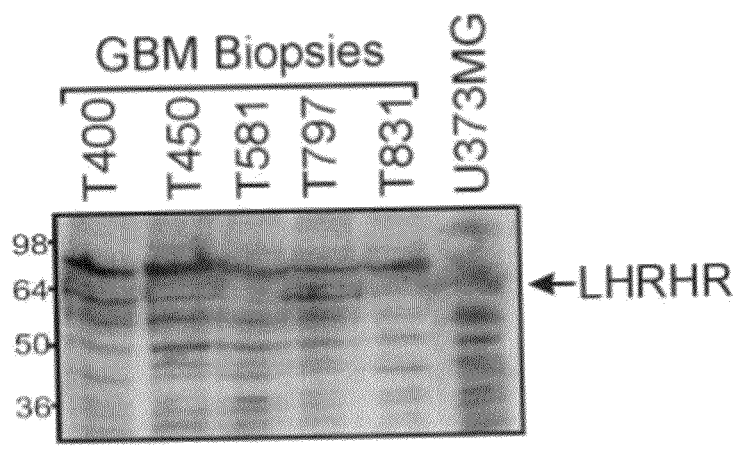

The Western blotting results demonstrated that GnRH receptors were present in all five glioblastomas analyzed (FIG. 13) and in five glioblastoma biopsies (FIG. 14). The membrane fractions of these tumors revealed distinct bands at approximately 64 kD.

Figure 15:
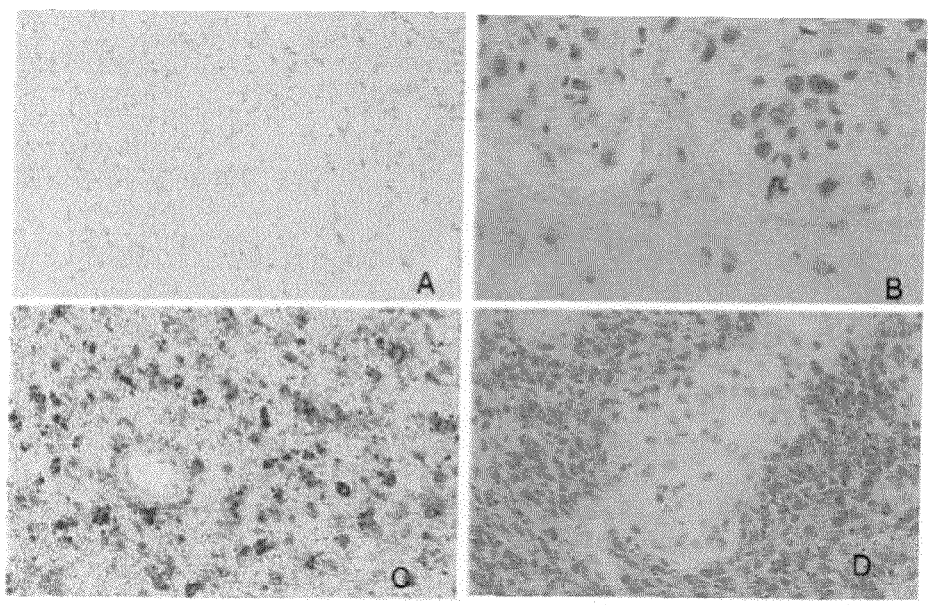
FIG. 15: Immunohistochemical staining for the GnRH (LHRH) receptor. (A) A weak positive result is observed in scattered neurons of the normal cerebral cortex (right). (B) Reactive astrocytes (bottom) around metastatic carcinoma (top) exhibit faint immunoreactivity in the cell membrane. (C) Marked immunostaining is present in tumor cells but not in vascular cells (center) of fibrillary astrocytoma. (D) A glioblastoma exhibits marked staining for GnRH receptor, whereas the hyperplastic vessel (center) is negative.

Through standard immunohistochemistry techniques, we demonstrated that all astrocytomas and glioblastomas strongly express GnRH receptor (FIG. 15). Most tumor cells exhibit a punctate staining pattern, while a few tumor cells show diffuse cytoplasmic staining. Blood vessels stained negative, including the abnormal vascular proliferations typical of glioblastomas. In the normal adult brain, the most intense staining is observed in the scattered cells of the adenohypophysis. In the cerebral cortex, a few neurons and perivascular astrocytes weakly express GnRH receptors. A higher number of positive neurons are observed in hippocampus and cerebellum tissues, while no immunoreactivity is seen in white matter and basal ganglia. Choroid plexus epithelial cells revealed strong staining, but ependymal cells were negative. Interestingly, most reactive astrocytes show a marked upregulation of GnRH receptor in the cell membrane, as demonstrated in the brain tissue surrounding metastatic carcinomas. Staining of reactive astrocytes is distinct but generally weaker than that of neoplastic astrocytes.

Effect of a GnRH Agonist on Glioblastoma Cell Proliferation

The observation that GnRH receptors are expressed in U-87 cells, both at mRNA and protein levels, prompted us to investigate the role of these receptors in the regulation of glioblastoma cell proliferation. Treatment of U-87 cells with a potent GnRH agonist (ZOLADEX®) results in a significant decrease of the proliferation rate, ZOLADEX® being significantly effective at doses ranging from $10^{-8}$ to $10^{-6}$ M (FIG. 12C). The ZOLADEX® concentration of $10^{-8}$M causes about 23% inhibition versus controls; ZOLADEX® concentration of $10^{-6}$M causes about 45% inhibition versus controls. The anti-proliferative effect of ZOLADEX® on U-87 is comparable to that previously observed in 1994 on prostate cancer cells DU145 by Dondi et al., Cancer Res, 1994; 54: 4091-4095.

The data reported here demonstrates for the first time that GnRH receptors are expressed in glioblastoma U-87MG cells and in glioblastoma tumor specimens, and that their activation by means of a potent GnRH agonist brings about a dose-dependent decrease of cell proliferation. The presence of GnRH receptors negatively involved in the control of some types of cancer cell proliferation, but not those cancer cell types presently described, has already been reported (Emons G, Muller V, Ortmann O, Schulz K-D. Effects of LHRH analogues on mitogenic signal transduction in cancer cells. J Steroid Biochem Molec Biol 1998; 65:199-206; Imai A, Tamaya T. GnRH receptor and apoptotic signaling. Vit Horm 2000; 59:1-33; Rambaldi A, Young D C, Griffin J D. Expression of the M-CSF (CSF-1) gene by human monocytes. Blood 1987; 69:1409-1413).

However, as mentioned, these functional studies have been performed only on epithelial-derived tumors, such as prostate, breast, ovarian and endometrial cancer and not in the cell types that are contemplated by the present invention since it was not known, or even predicted, that GnRH receptors could be present on these cell types. (Dondi et al, Cancer Res, 1994; 54: 4091-4095; Emons G, Muller V, Ortmann O, Schulz K-D. Effects of LHRH analogues on mitogenic signal transduction in cancer cells. J Steroid Biochem Molec Biol 1998; 65:199-206; Imai A, Tamaya T. GnRH receptor and apoptotic signaling. Vit Horm 2000; 59:1-33; Rambaldi A, Young D C, Griffin J D. Expression of the M-CSF (CSF-1) gene by human monocytes. Blood 1987; 69:1409-1413) GnRH agonists are widely and successfully used for the treatment of hormone-related cancers, mainly based on their ability to suppress the activity of the pituitary-gonadal axis. (Crawford E D, De Antonio E P, Labrie F, Schroder F H, Geller J. Endocrine therapy of pro static cancer: optimal form and appropriate timing. J Clin Endocrinol Metab 1995; 80:1062-1078. Manni A. Hormonal approaches to the chemoprevention of endocrine-dependent tumors. Endocr-Rel Cancer 1999; 6:483-485).

The present observations that these above-discussed compounds are capable of exerting an additional, more direct antiproliferative effect at the level of the tumor cell gives further support and meaning to the utility of these GnRH analogues for the treatment of these neoplasms. This study represents the first report of an inhibitory activity of GnRH agonists on the in vitro proliferation of glioblastoma cells expressing the GnRH receptor. Our finding of GnRH receptor up-regulation in tumor cells as compared to non-neoplastic astrocytes confirms our hypothesis that the presence of GnRH receptors can be considered as a diagnostically useful marker in gliomas. The data also disclose that GnRH receptors represent a molecular target for a successful hormonal therapeutic approach, based on the application of GnRH agonists either alone, or in a combination with the GnRH antagonists described above.

Figure 16:
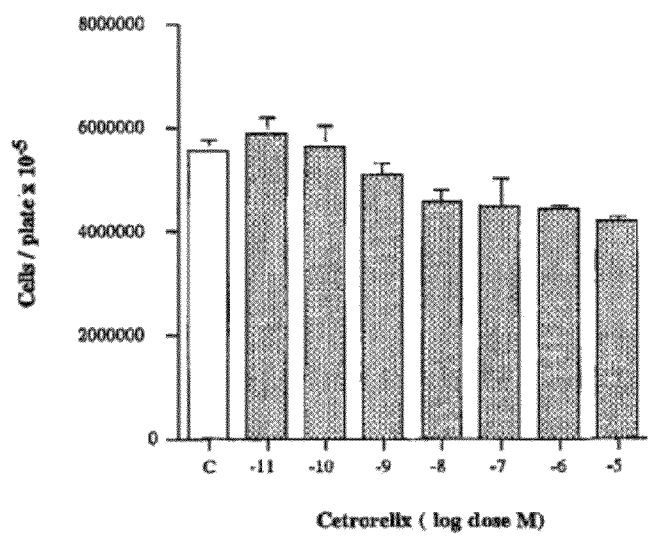
FIG. 16: Effects of the GnRH antagonist Cetrorelix® on the proliferation of human glioblastoma U-87MG (U-87) cells. Results are expressed as mean cell number per plate±SE. *, $p<0.05$ vs. control (C).

Our observation confirming that GnRH receptors are expressed in U-87MG (U-87) cells, both at the mRNA and protein levels, prompted us to investigate the role of these receptors in the regulation of glioblastoma cell proliferation. Treatment of U-87MG cells with Cetrorelix® results in a marked decrease of the cellular proliferation rate, namely at a $10^{-6}$ M dosage, Cetrorelix® decreased proliferation by 28%, while at a $10^{-5}$ M dosage, Cetrorelix® showed 30% inhibition of proliferation compared to controls. The results of this study are depicted in FIG. 16. These observations are consistent with anti-proliferative effects shown using the GnRH agonist ZOLADEX® on U-87 cells, as discussed above, and are further comparable to previous observations following the application of ZOLADEX® on the human epithelial ovarian cancer cell line, EFO-21 (Emons et al., Cancer Res, 1993, 53: 5439-46).

Example 18

The Human Erythropoietin (hEPO) Receptor is Co-Expressed with the GnRH Receptor in Glioblastoma, Melanoma, and Human Meningeoma Cells Erythropoietin (EPO) is the primary regulator of erythropoiesis, stimulating growth, preventing apoptosis, and promoting differentiation of red blood cell progenitors. The EPO receptor belongs to the cytokine receptor superfamily. EPO and its receptor have been localized in several nonhematopoietic tissues and cells, including the liver, the uterus, the central nervous system (CNS), vascular endothelial cells, and solid tumors. These findings have led researchers to explore the role of EPO in nonhematopoietic tissues and its potential use outside erythropoiesis, including its use in CNS disorders (Lappin T. The cellular biology of erythropoietin receptors. The Oncologist 2003:8(suppl 1):15-18). Moreover, these observations prompted us to specifically investigate whether the human erythropoietin receptor (hEPO-R) was in fact expressed in certain tumor types where such expression has not been characterized to date.

Figure 17A:
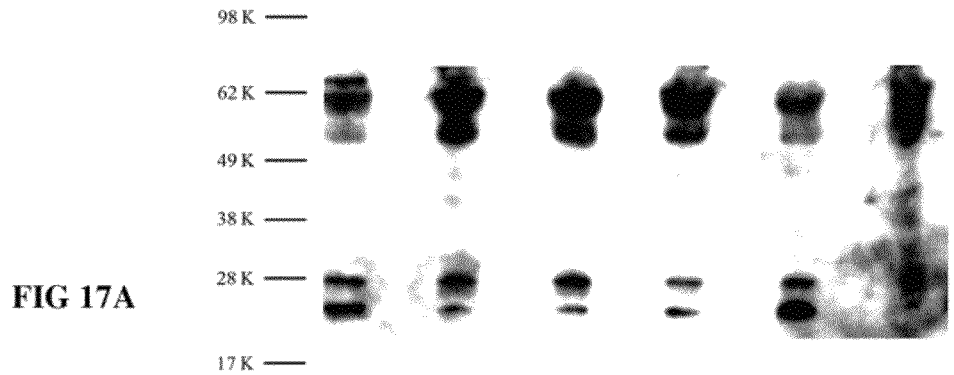
FIG. 17: Western blot of membrane fractions showing the presence of erythropoietin (EPO) protein: (A) derived from three human glioblastoma biopsy samples (termed GB1, GB3 and GB4), four human melanoma biopsy samples (termed MN1, MN2, MN3 and MN5) and (B) three human meningeoma biopsy samples (MG1, MG2 and MG3), respectively. All samples show a clearly visible band at a size (in kD) corresponding to the EPO receptor protein.
Figure 17B:
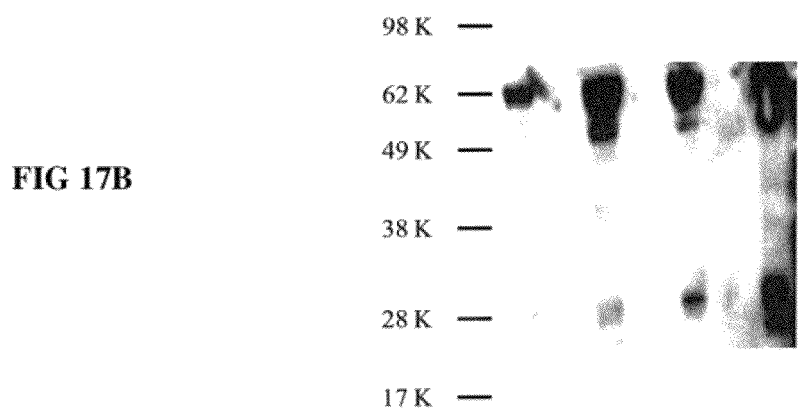
Figure 18A:
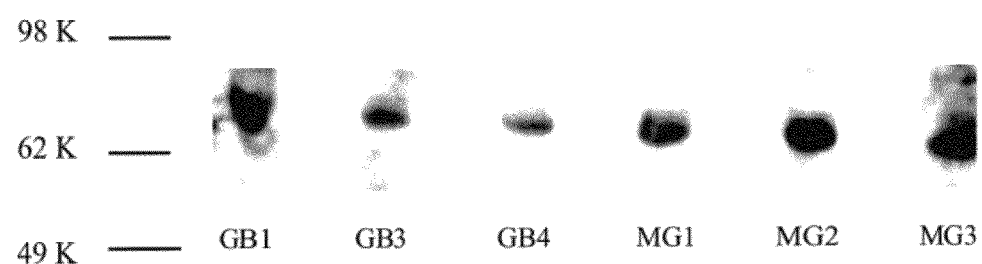
FIG. 18: Western blot of membrane fractions showing the presence of erythropoietin receptors (EPO-R): (A) derived from three human glioblastoma biopsy samples (termed GB1, GB3 and GB4), four human melanoma biopsy samples (termed MN1, MN2, MN3 and MN5) and (B) three human meningeoma biopsy samples (MG1, MG2 and MG3), respectively. All samples show a clearly visible band at a size (in kD) corresponding to the EPO receptor.
Figure 18B:
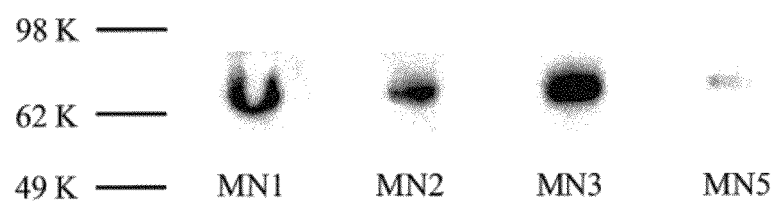
Figure 19A:
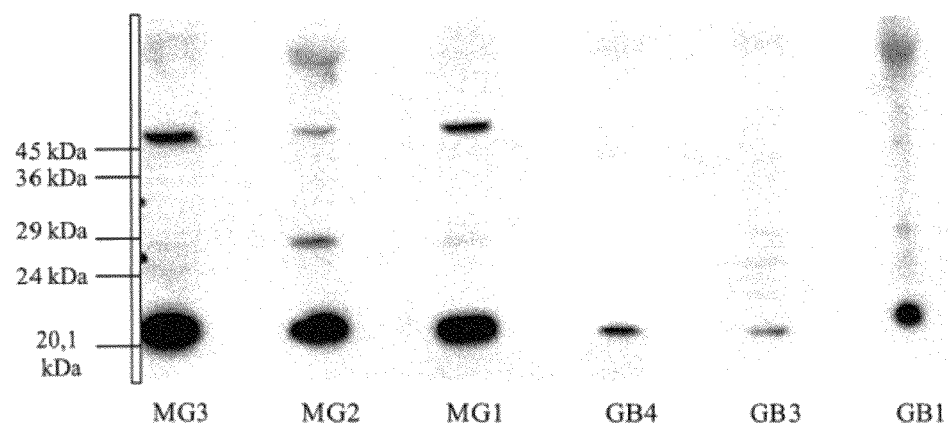
FIG. 19: Western blot of membrane fractions showing the presence of GnRH receptors: (A) derived from three human glioblastoma biopsy samples (termed GB1, GB3 and GB4), four human melanoma biopsy samples (termed MN1, MN2, MN3 and MN5) and (B) three human meningeoma biopsy samples (MG1, MG2 and MG3), respectively. All samples show a clearly visible band at a size (in kD) corresponding to the GnRH receptor.
Figure 19B:
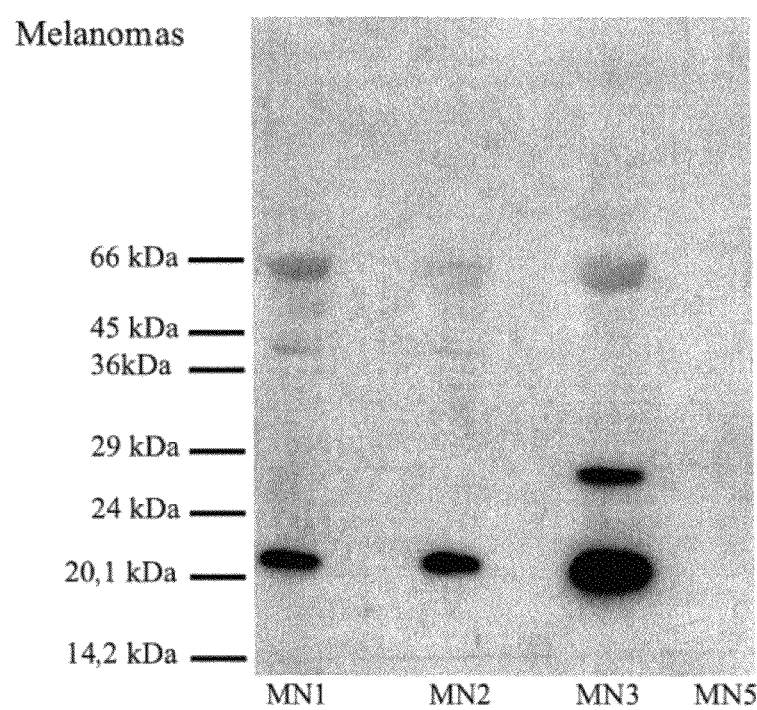

Accordingly, we have conducted protein characterization studies by performing a Western blot analysis of membrane fractions derived from three human glioblastoma biopsy samples (termed GB1, GB3 and GB4), four human melanoma samples (termed MN1, MN2, MN3 and MN5) and three human meningeoma samples (MG1, MG2 and MG3), respectively. Cells were harvested for total cell lysate using RIPA buffer (1% Nonidet P-40, 0.5% sodium deoxycholate, 0.1% SDS, 50 mM Tris-HCl, pH 7.5) containing a protease inhibitor mixture (Roche Diagnostics GmbH, Mannheim, Germany), as well as 1 mM NaF and 1 mM NaVO$_4$. The lysates (30 μg) were denatured in the sample buffer and then subjected to 4-15% SDS-PAGE gel electrophoresis followed by Electrotransfer to polyvinylidene difluoride membrane. The Anti-EPO-R antibody (and others not specified) was obtained from Santa Cruz Biotechnology (Santa Cruz, Calif.). As can be clearly observed from Figures, each of these cell types showed clearly visible bands at a size (in kD) corresponding to EPO protein (at about 66 kD; FIG. 17A, FIG. 17B) and the EPO receptor (at about 65 kD; FIG. 18A, FIG. 18B) in addition to showing a band that corresponds to the GnRH receptor (at about 66 kD, with an additional tumor isoform shown at 20.1 kD; FIG. 19A, FIG. 19B).

The data reported here demonstrates for the first time that GnRH receptors and hEPO receptors are surprisingly co-expressed together, simultaneously, in all of the human tumor specimens presently examined. Furthermore, their parallel occurrence at precisely the same stage of tumor growth is part of a clinical pathology whereby both receptor types appear to be intact and functional.

Our findings also provide evidence for the first time that conjugates and/or combination treatments of the above tumor types (confirmed to be GnRH receptor-positive) with a conjugate of GnRH analogue, wherein the analogue is a GnRH agonist or antagonist, in addition to erythropoietin (EPO) analogues, wherein the EPO analogue is an hEPO agonist or hEPO antagonist offers a viable and effective option of treatment for patients afflicted with these tumor types.

The present invention additionally provides that these treatment methods can be accomplished by treatment using conventional methods, namely through the use of a nanoparticle, wherein said particle contains an hEPO analogue and a GnRH analogue (a suitable solid lipid nanoparticle is described in U.S. Pat. Nos. 5,889,110, 6,419,949 and in U.S. patent application Ser. Nos. 10/506,952 and 10/451,985). Moreover, the treatment methods may be carried out in a similar manner using a magnetic nanoparticle according to U.S. Pat. No. 6,514,481.

Example 19

A Combination Treatment Using the GnRH Receptor Agonist Nafarelin with a hEPO Receptor Agonist Causes a Significant Increase of Apoptosis in Glioblastoma Cells Compared to Controls or Each Compound Administered Alone As described above, U-87MG cells are known in the literature to have hEPO receptors, thus we wanted to further explore a possible role of these receptors in inducing and/or mediating apoptosis in this cell type to thereby inhibit cell viability. The cells were cultured as above, and then subjected to three separate experiments wherein was applied at increasing concentrations of $10^{-6}$M, $10^{-5}$M and $10^{-3}$M and the hEPO was applied at increasing concentrations of 0.1 U/ml, 1 U/ml, 10 U/ml and 20 U/ml for 72 hours.

Measurement of the percentage of apoptotic events in the U-87MG cells was performed by determining the electric mitochondrial membrane potential in connection with Tetramethyl Rhodamine Methyl Ester (TMRM) fluorescence using a high-resolution single-cell confocal microscopy cytofluorometer (Floryk D. & Houstek J. (1999): Tetramethyl rhodamine methyl ester (TMRM) is suitable for cytofluorometric measurements of mitochondrial membrane potential in cells treated with digitonin, In: Bioscience Reports. Bd. 19, Nr. 1, S. 27-34). These measurements were compared with those made on these cells prior to treatment with the compounds and the incidence of apoptosis was dramatically increased following U-87MG cell exposure to Nafarelin and hEPO (as depicted in Table III below).

Figure 20A:
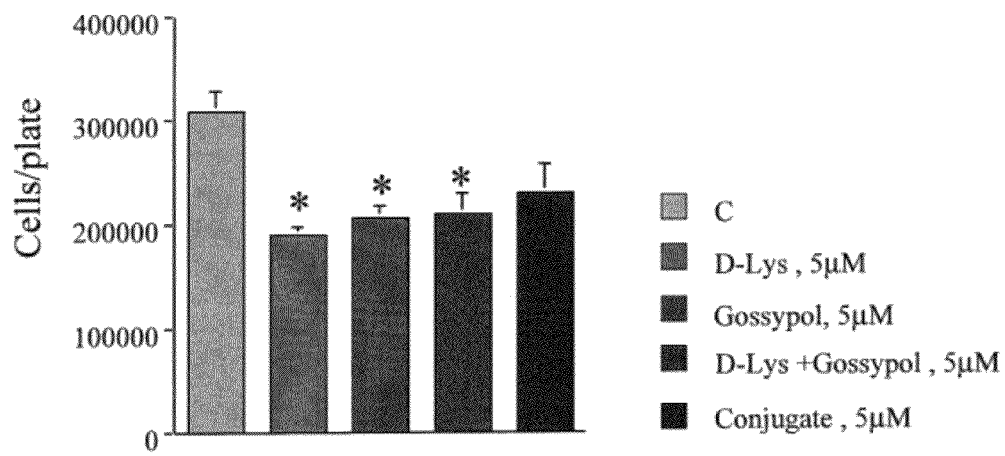
FIG. 20: (A) Effects of the GnRH agonists (D-Lys6)-GnRH, Gossypol, the combination of D-Lys6-GnRH and racemic Gossypol, and (B) a (D-Lys6)-GnRH conjugate, and (C) racemic Gossypol alone on the proliferation of BLM human melanoma cells. Results are expressed as mean cell number per plate±SE. *, p<0.05 vs. control (C).
Figure 20B:
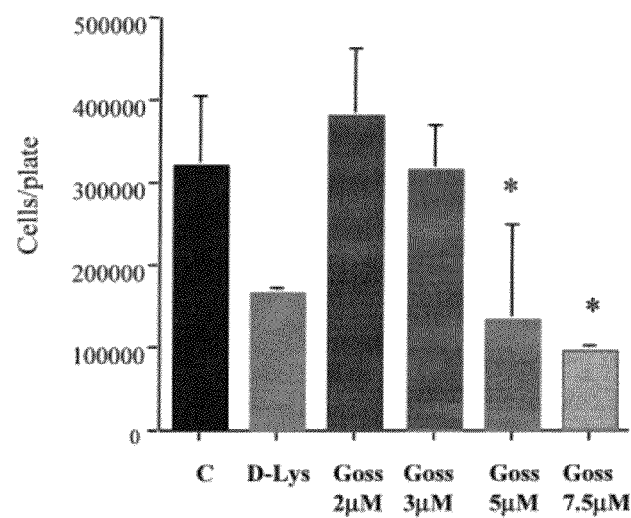
Figure 20C:
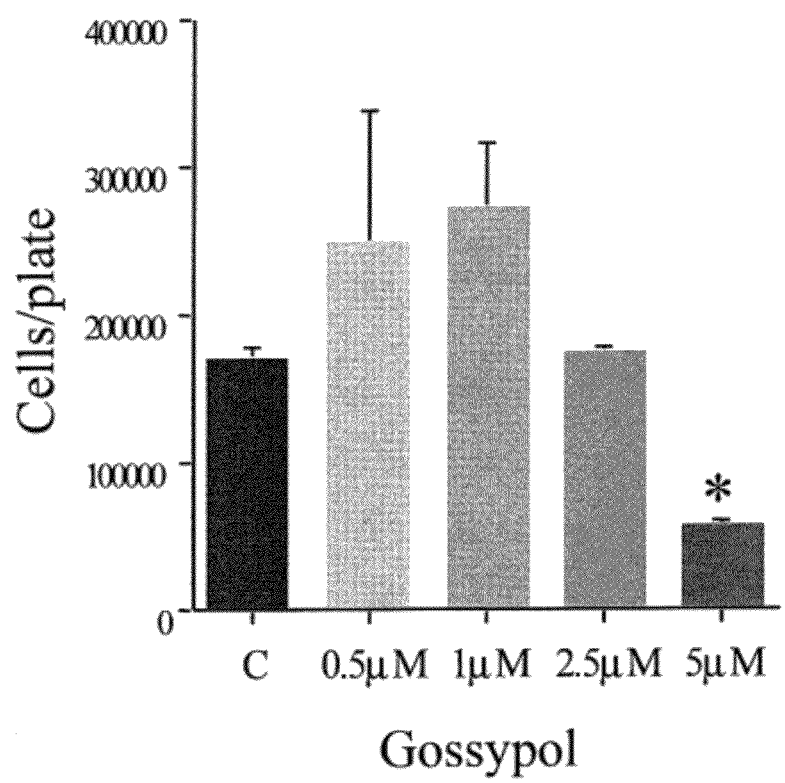

The effects of the GnRH agonist (D-Lys6)-GnRH, Gossypol, the combination of D-Lys6-GnRH and racemic Gossypol, and a conjugate of (D-Lys6)-GnRH, and racemic Gossypol alone on the proliferation of BLM human melanoma cells are depicted in FIG. 20 (A), (B) and (C), respectively. Results are expressed as mean cell number per plate±SE. *, p<0.05 vs. control (C).

In more detail, a (D-Lys6)-GnRH concentration of $5 \times 10^{-5}$ M resulted in a 39% inhibition of cellular proliferation ver-

TABLE III

Treatment of the human glioblastoma cell line U-87 with increasing concentrations of Nafarelin and EPO, and combinations thereof, with the corresponding impact on apoptosis events, expressed as a %.

| Treatment Compound | Concentration Used | | | | |
|---|---|---|---|---|---|
| Nafarelin | 0 | $10^{-6}$ M | $10^{-5}$ M | | $10^{-3}$ M |
| | 14.065 ± 0.7425 | 11.66 ± 0.5374 | 17.885 ± 1.223 | | 24.71 ± 0.3111 |
| hEPO | 0 | 0.1 U/ml | 1 U/ml | 10 U/ml | 20 U/ml |
| | 14.065 ± 0.7425 | 14.75 ± 4.801 | 15.89 ± 1.754 | 20.32 ± 1.068 | 18.25 ± 3.613 |
| Nafarelin + hEPO | 0 | $10^{-5}$ M + 1 U/ml | $10^{-5}$ M + 10 U/ml | | $10^{-4}$ M + 10 U/ml |
| | 14.065 ± 0.7425 | 19.75 ± 0.3536 | 23.20 ± 0.9617 | | 28.10 ± 0.1838 |

All proliferation experiments were performed in four to six replicates. The data obtained from three independent experiments were analyzed according to the Dunnett's test following a one-way ANOVA analysis. Percentage of cells exhibiting apoptosis±SE. *, p<0.05 vs. control (C).

The above results confirm that a combined treatment of the GnRH receptor agonist Nafarelin with a human Erythropoietin receptor agonist causes a more powerful effect in increasing apoptosis in U-87MG glioblastoma cells compared to controls or each compound administered alone. Moreover, hEPO was shown to exert an apoptosis effect on the U-87MG tumor cells at concentrations higher than 10 U/ml but at concentrations of 0.1 U/ml hEPO, no significant anti-proliferative effect on these cells was presently observed.

The apoptosis effect resulting from the high dosages of hEPO, especially in a combination with a GnRH analogue is surprising since hEPO is well known in the art to actually exert a general stimulatory effect on tumor cell proliferation, and importantly, including U-87MG cells (I. Hassouna, et al. Erythropoietin Augments Survival of Glioma Cells After Radiation and Temozolomide, International Journal of Radiation Oncology Biology Physics, 2008, Volume 72, Issue 3, Pages 927-934).

Additionally, we investigated the effects of these compounds on the activity of the enzyme caspase, in particular caspase 3. Caspase-3 cleavage, which contributes to the induction of apoptosis, was shown to be significant compared to controls, as measured by immunofluorescence staining (results not shown).

Example 20

The GnRH Agonist (D-Lys6)-GnRH and LH Inhibitor Gossypol, and Combinations thereof Show Pronounced Anti-proliferative Effects on Human Melanoma Cells In addition to the various GnRH agonists previously investigated according to the present invention, we wanted to explore the anti-proliferative effects of the GnRH peptide analogue (D-Lys6)-GnRH on human melanoma cells. Furthermore, the anti-proliferative effects of the LH inhibitor and potent contraceptive agent, Gossypol, either alone or conjugated to (D-Lys6)-GnRH, were also considered.

sus controls. The anti-proliferative effect of (D-Lys6)-GnRH is thus comparable to that described above for ZOLADEX®, and even more pronounced than that observed for Cetrorelix®. Moreover, racemic Gossypol exerted pronounced anti-proliferative effects on BLM melanoma cells. The L-Gossypol molecule is well known to be the active moiety of racemic Gossypol; the D-Gossypol racemate isoform is known not to have any impact on tumor cell activity, thus the present (D-Lys6)GnRH conjugate construct included the L-Gossypol entity. An additional, more potent Gossypol derivative, namely Apogossypolone, is also suitable for use in conjugation with (D-Lys6)GnRH for these studies.

The present results demonstrate that a first construct comprising a conjugate based on two Gossypol molecules, and of one molecule of (D-Lys6)GnRH yields a pronounced anti-proliferative effect on BLM melanoma tumor cells. This anti-proliferative effect is comparable with that observed using a combination of racemic gossypol and (D-Lys6)-GnRH on BLM melanoma tumor cells. It is known that the clinical toxicity associated with such a conjugate can be minimized, which makes clinical applicability more attractive compared to use of the compounds individually given their known toxicity. These results are additionally surprising in view of the fact that previous studies showed that (Lys6)-GnRH failed to demonstrate any effect on tumor cell proliferation either in vitro or in vivo (See Keller et al., IND 2009, Cancer Res, 2005; 65 (13) 5857-63).

Example 21

The GnRH Agonist ZOLADEX® Reduces Tumor Weight Following Application to Nude Mice Bearing Human Melanoma Tumor Xenotransplants According to the present invention, the GnRH agonist ZOLADEX® exerts a significant anti-proliferative effect on tumor cells, such as melanoma cells, bearing GnRH-receptors. Moreover, other GnRH peptide agonists, for example, Nafarelin (D-Lys6)-GnRH II and the GnRH antagonist Cetrorelix, either individually or in a combination, have been presently shown to retard the proliferation of the described tumor cell, thereby decreasing the potential of these cells to become malignant. These observations prompted us to investigate further anti-proliferative roles, and other effects, resulting from intermittent or parallel treatment using two different GnRH agonist compounds, and GnRH agonists in combination with various GnRH antagonists described herein.

Exemplary compound combinations investigated included a GnRH agonist and a GnRH antagonist, two GnRH antagonists, or two GnRH agonists. The agonist or antagonist can vary in name and molecular form depending on the GnRH receptor status. That is, if the tumor tissue demonstrates GnRH receptor depletion following treatment, a combination treatment can be administered using at least one or more GnRH antagonists, such as IN3 and Cetrorelix, or IN3 and ANT 135-25, or a combination of IN3 and (D-Lys6)GnRH II.

In one series of experiments, nude mice bearing human melanoma tumor cell line xenotransplants were treated for two weeks with 100 μg of Goserelin daily, while a second group of mice was administered 200 μg of Goserelin daily, with an additional daily supplement given by subcutaneous injection. After two weeks, a significant 50% reduction in tumor weight was observed in both groups of nude mice. The in vivo tumor growth has three predominant characteristics: mitotic activity, dedifferentiation, and infiltration of cells into the surrounding tissue and vessels.

Figure 21:
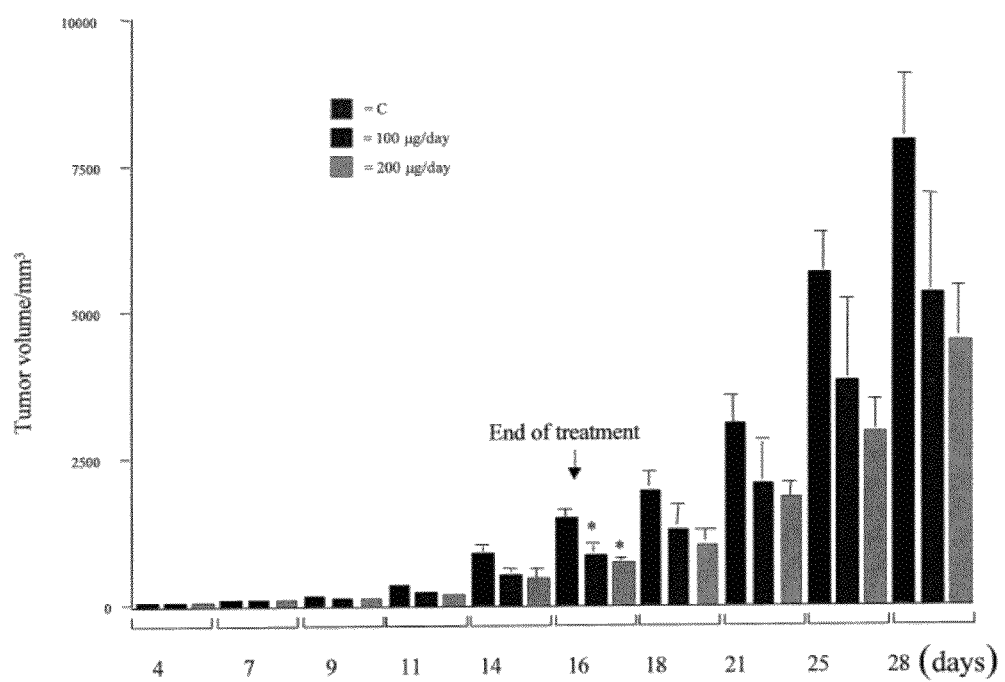
FIG. 21: Anti-proliferative effects of ZOLADEX® on the growth of BLM human melanoma xenografts in nude mice.

The observed reduction in tumor weight demonstrates a clear anti-proliferative effect through an inhibition of growth of the BLM melanoma tumor cell line implant by the administered Goserelin, as further supported by the persistence of tumor growth inhibition for a period of almost 4 weeks, despite the cessation of the treatment with 100 μg/day of ZOLADEX® or the 200 μg/day dosage, which yielded an even more powerful growth inhibitory effect on these cells. Results for this study are depicted in FIG. 21. These observations are in line with the previously shown inhibition of Matrigel invasion of BLM cells under Zoladex treatment, as described above. A histological investigation of the tumor before and after treatment has confirmed this finding (results not shown).

Although ZOLADEX® was found to inhibit BLM cell growth by about 50%, but without causing a full tumor remission in the BLM xenotransplanted nude mice, we were prompted to investigate alternative methods of treatment for the GnRH-receptor bearing tumors described herein. For example, the tumors may receive a combination of GnRH analogues, or alternatively, a combination of a GnRH analogue with human gonadotropin inhibiting hormone, or as a conjugate with a cytotoxic tumor cell killing agent including doxorubicin, L-Gossypol, Gossypolone, Apogossypolone, Rose Bengal, MRA-CN, paclitaxel (Taxol®), Hypericin, Hyperforin, or Emodin. Additionally, a GnRH analogue may also be applied to the tumors cells in combination with other compound, including, for example, anti-angiogenic substances such as endothelin antagonists, zibotentan or thrombopoietin peptide agonists, TPO peptide mimetics such as Fab 59, AMG 531, Peg-TPOmp or a non peptide EPO mimetic such as Eltrombopag (SB497115, Promacta) or AKR-501. Moreover, these treatment compounds can be applied through the use of a nanoparticle, wherein said particle contains the combination compound or carried out using a magnetic nanoparticle as described above.

In another set of experiments, ZOLADEX® treatment was administered to mice for a period of four to eight weeks, with an additional GnRH antagonist treatment to avoid any tumor proliferation (i.e. flare up) following cessation of the therapy and to avoid tumor cell receptor depletion. Despite maintaining a relative tumor growth inhibition, a rebound of tumor growth (flare up) is observed after two weeks (16 days) of ZOLADEX® treatment once said treatment has stopped.

A more effective method is to commence IN3 (a non-peptide GnRH antagonist) treatment following 4-8 weeks of treatment with ZOLADEX®, which causes the induction of GnRH receptors (US Patent Application No. 20050203019 or Ser. No. 11/050,662). However, IN3 has not been known as an inhibitor of tumor growth, and has not, until now, been described as an effective pharmacochaperone on GnRH receptors (and their isoforms) in human tumors as disclosed by the present invention. This treatment protocol can be followed-up by assessing tumor recidivation and receptor determination by removal of tumor tissue or CSF or plasma (e.g. via lumbar puncture, a blood sample, a urine sample in conjunction with a determination of PCR or RT-PCR products of the tumor cell GnRH receptor) in case of persistent tumor growth or tumor recurrence. After IN3 treatment, an additional four-week regimen of ZOLADEX® administration, or alternatively, Cetrorelix or ANT 135-25 administration can follow, after which the IN3 treatment restarts for a further two weeks in order to cause GnRH receptor induction.

Example 22

A GnRH Agonist Combined with a Cytotoxic Conjugate Reduces Tumor Weight Following Application to Nude Mice Bearing Human Small Cell Lung Tumor Xenotransplants In another series of experiments, nude mice bearing human small cell lung carcinoma tumor cell line xenografts (a model that is described by Nemati et al. Distinctive Potentiating Effects of Cisplatin and/or Ifosfamide Combined with Etoposide in Human Small Cell Lung Carcinoma Xenografts, Clinical Cancer Research Vol. 6, 2075-2086, 2000), are treated with a cytotoxic conjugate as described by the present invention, using an experimental procedure and dosage similar to those previously known (Keller et al., supra). The cytotoxic substance, which is coupled or conjugated with, for example, (D-Lys6)-GnRH or with (D-Lys6)-GnRH II, is Doxorubicin (AN-152), 2-pyrrolinodoxorubicin (AN-207), Daunorubicin, L-Gossypol, Apogossypolone, Rose Bengal, Hypericin, Hyperforin, MRA-CN, or Docetaxel (Taxol®).

Significant anti-proliferative effects were observed in this model, similar to effects previously reported for xenografts derived from the human melanoma tumor lines MRI-H255 and MRIH187 (Keller et al, supra), where the present tumor inhibitory effects are observed as a reduction in tumor volume and/or in weight in vivo. Analyses using RT-PCR and Western-Blot techniques yielded results similar to those observed with the glioma and melanoma biopsies as described above.

Example 23

A GnRH Agonist or a GnRH Antagonist Combined with an Anti-angiogenic Compound Results in Increased Apoptosis in Human Small Cell Lung Cancer Cell Lines In another aspect of the invention, human small cell lung cancer cell lines NCI-H1688, NCI H1417, NCI H1672, NCI-H1836, DMS 79, DM 553, DMS 114, SW 1271, NCI-H 2227, NCI-H I 1963 and SHP-77 and multidrug resistant small cell lung carcinoma cell line H 69 AR are each cultured using techniques as described above for the U-87 cell line, and then treated at those dosages presently described for the GnRH agonists (D-Lys6)-GnRH, Goserelin, Triptorelin, Leuprolide, Buserelin, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH II and Lamprey GnRH III or with the presently described GnRH antagonists such as Ac-D-Nal(2)-D-4-ClPhe-D-Pal-Ser-1-MePal-D-IsopropylLys-Leu-IsopropylLys-Pro-D-AlaNH$_2$ (also known as Ant 135-25; the Mepal portion is known as 1-Methyl-3-[3'-pyridyl]-alanine), Teverelix (also known as Antarelix®), Cetrorelix (also known as Cetrotide®), Abarelix (also known as Plenaxis®), D-63153 (also known as Ozarelix®), acyline, azaline B, antide (also known as Iturelix®), Degarelix (FE200486), Ganirelix, Nal-Glu, Orntide (also known as Ornirelix®) or with antagonist peptidomimetic ((2S)-2-[5-[2-(2-azabicyclo[2,2,2]oct-2-yl)-1,1-dimethyl-2-oxoethyl]-2-(3,5-dimethylphenyl)-1H-indol-3-yl]-N-(2-pyridin-4-ylethyl-)propan-1-amine (also known as "IN3").

The above described GnRH agonist or GnRH antagonist is administered in a combination with erythropoietin mimetic peptide (EMP-1) or a dimer of EMP-1 or a biologically functional derivative of EMP-1 or with a peptide thrombopoietin mimetic (TPO), a peptide mimetic Fab 59, AMG 531 or Peg-TPOmp, wherein the combination results in a significant increase of apoptosis in these cell lines as compared to controls or when each compound is administered alone.

Example 24

A GnRH Agonist or a GnRH Antagonist Combined with an Endothelin Antagonist Results in Increased Apoptosis and Anti-proliferation in Human Small Cell Lung Cancer Cell Lines In another aspect of the invention, human small cell lung cancer cell lines NCI-H1688, NCI H1417, NCI H1672, NCI-H1836, DMS 79, DM 553, DMS 114, SW 1271, NCI-H 2227, NCI-H I 1963 and SHP-77 and multidrug resistant small cell lung carcinoma cell line H 69 AR are each cultured using techniques as described above for the U-87 cell line, and then treated at those dosages presently described for the GnRH agonists (D-Lys6)-GnRH, Goserelin, Triptorelin, Leuprolide, Buserelin, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH II and Lamprey GnRH III or with the presently described GnRH antagonists such as Ac-D-Nal(2)-D-4-ClPhe-D-Pal-Ser-1-MePal-D-IsopropylLys-Leu-IsopropylLys-Pro-D-AlaNH$_2$ (also known as Ant 135-25; the Mepal portion is known as 1-Methyl-3-[3'-pyridyl]-alanine), Teverelix (also known as Antarelix®), Cetrorelix (also known as Cetrotide®), Abarelix (also known as Plenaxis®), D-63153 (also known as Ozarelix®), acyline, azaline B, antide (also known as Iturelix®), Degarelix (FE200486), Ganirelix, Nal-Glu, Orntide (also known as Ornirelix®) or with antagonist peptidomimetic ((2S)-2-[5-[2-(2-azabicyclo[2,2,2]oct-2-yl)-1,1-dimethyl-2-oxoethyl]-2-(3,5-dimethylphenyl)-1H-indol-3-yl]-N-(2-pyridin-4-ylethyl-)propan-1-amine (also known as "IN3").

The above described GnRH agonist or GnRH antagonist is administered in a combination with the endothelin antagonist Zibotentan (3-pyridinesulfonamide, N-(3-methoxy-5-methyl-2-pyrazinyl)-2-[4-(1,3,4-oxadiazol-2-yl)phenyl]- or N-(3-methoxy-5-methylpyrazin-2-yl)-2-[4-(1,3,4-oxadiazol-2-yl)phenyl]pyridine-3-sulfonamide) at increasing concentrations from $10^{-8}$M to $10^{-4}$M, wherein the combination results in a significant increase of apoptosis and anti-proliferative effects in these cell lines as compared to controls in a manner reported above for the U-87 cell line.

Example 25

A GnRH Agonist or a GnRH Antagonist Combined with a Human Gonadotropin Inhibiting Hormone Peptide Results in Increased Apoptosis and Anti-proliferation in Human Small Cell Lung Cancer Cell Lines In another aspect of the invention, human small cell lung cancer cell lines NCI-H1688, NCI H1417, NCI H1672, NCI-H1836, DMS 79, DM 553, DMS 114, SW 1271, NCI-H 2227, NCI-H I 1963 and SHP-77 and multidrug resistant small cell lung carcinoma cell line H 69 AR are each cultured using techniques as described above for the U-87 cell line, and then treated at those dosages presently described for the GnRH agonists (D-Lys6)-GnRH, Goserelin, Triptorelin, Leuprolide, Buserelin, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH II and Lamprey GnRH III or with the presently described GnRH antagonists such as Ac-D-Nal(2)-D-4-ClPhe-D-Pal-Ser-1-MePal-D-IsopropylLys-Leu-IsopropylLys-Pro-D-AlaNH$_2$ (also known as Ant 135-25; the Mepal portion is known as 1-Methyl-3-[3'-pyridyl]-alanine), Teverelix (also known as Antarelix®), Cetrorelix (also known as Cetrotide®), Abarelix (also known as Plenaxis®), D-63153 (also known as Ozarelix®), acyline, azaline B, antide (also known as Iturelix®), Degarelix (FE200486), Ganirelix, Nal-Glu, Orntide (also known as Ornirelix®) or with antagonist peptidomimetic ((2S)-2-[5-[2-(2-azabicyclo[2,2,2]oct-2-yl)-1,1-dimethyl-2-oxoethyl]-2-(3,5-dimethylphenyl)-1H-indol-3-yl]-N-(2-pyridin-4-ylethyl-)propan-1-amine (also known as "IN3").

The above described GnRH agonist or GnRH antagonist is administered in a combination with a human Gonadotropin inhibiting hormone peptide such as RFamide-related peptide-3 or RFamide related peptide-1, wherein the combination results in a significant increase of apoptosis and anti-proliferative effects in these cell lines as compared to controls in a manner reported above for the U-87 cell line and those experiments performed using the combination of hEPO and Nafarelin in glioblastoma cells.

Example 26

A GnRH Agonist or a GnRH Antagonist Combined with an Anti-angiogenic Compound Results in Increased Apoptosis and Anti-proliferation in Human Glial Cell Lines In another aspect of the invention, human glial cells in culture are prepared using known methods (van Noor et al. Drug Discovery Today, Volume 11, (1-2) (2006) 74-80), and then treated at those dosages presently described for the GnRH agonists (D-Lys6)-GnRH, Goserelin, Triptorelin, Leuprolide, Buserelin, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH II and Lamprey GnRH III or with the presently described GnRH antagonists Cetrorelix (also known as Cetrotide®), Ant 135-25, or IN3.

The above described GnRH agonist or GnRH antagonist is administered in a combination with a peptide thrombopoietin mimetic (TPO), a peptide mimetic Fab 59, AMG 531 or Peg-TPOmp, or with a non-peptide EPO mimetic such as Eltrombopag (SB497115, Promacta), AKR-501 or with human erythropoietin or with an erythropoietin mimetic peptide such as EMP-1, wherein the combination results in a significant increase of apoptosis and anti-proliferative effects in these cell lines as compared to controls in a manner reported above for the U-87 cell line.

Example 27

A GnRH Agonist or a GnRH Antagonist Combined with an Endothelin Antagonist Results in Increased Apoptosis and Anti-proliferation in Human Glial Cell Lines In another aspect of the invention, human glial cells in culture are prepared using known methods (van Noor et al. Drug Discovery Today, Volume 11, (1-2) (2006) 74-80), and then treated at those dosages presently described for the GnRH agonists (D-Lys6)-GnRH, Goserelin, Triptorelin, Leuprolide, Buserelin, Lutrelin, Histrelin, Nafarelin, Azagly-Nafarelin, Deslorelin, Cystorelin, Decapeptyl, Gonadorelin, GnRH, D-Lys(6)-GnRH II, Lamprey GnRH II, (D-Lys6)-Lamprey GnRH II and Lamprey GnRH III or with the presently described GnRH antagonists Cetrorelix (also known as Cetrotide®), Ant 135-25, or IN3.

The above described GnRH agonist or GnRH antagonist is administered in a combination with the endothelin antagonist Zibotentan (3-pyridinesulfonamide, N-(3-methoxy-5-methyl-2-pyrazinyl)-2-[4-(1,3,4-oxadiazol-2-yl)phenyl]- or N-(3-methoxy-5-methylpyrazin-2-yl)-2-[4-(1,3,4-oxadiazol-2-yl)phenyl]pyridine-3-sulfonamide) at increasing concentrations from $10^{-8}$M to $10^{-4}$M, wherein the combination results in a significant increase of apoptosis and anti-proliferative effects in these cell lines as compared to controls in a manner reported above for the U-87 cell line.

For each of the above described combination embodiments, the treatment compounds can be applied through the use of a nanoparticle or a magnetic nanoparticle, wherein said particle contains the combination compound. In addition, the nanoparticle may be composed of a solid lipid and/or may be administered in the form of a nasal spray or in the form of intraocular application by injection or by means of eye drops, or in a parenteral manner.

The invention claimed is:

1. A method for selectively treating an ectodermally-originated tumor in a subject comprising:
   (a) selecting the subject on the basis of the subject having a positive detection and/or determination of GnRH receptors and/or GnRH receptor concentration in a sample of tumor cells derived from the tumor;
   (b) selectively administering to said subject a replication-decreasing amount of a compound comprising IN3 or a pharmacologically acceptable salt thereof sufficient to cause a detectable decrease in tumor replication through interaction with the positively-detected GnRH receptor; and
   (c) quantifying a decrease in tumor cell replication, wherein if tumor cell replication is not detected then selective administration of the compound is discontinued.

2. The method of claim 1, wherein the detecting and/or determining step (a) further comprises contacting the sample of the tumor cells with a GnRH receptor ligand and determining if binding occurred through a detection of the bound ligand.

3. The method of claim 2, wherein the sample of the tumor cells is derived from an ex vivo operatively excised tumor preparation or from an in vitro cellular culture based on said tumor preparations.

4. The method of claim 2, wherein the detecting the GnRH receptor is performed using immunohistochemistry, immunological methods including ELISA, measuring gene expression by detecting the quantity of cDNA produced from reverse transcription of GnRH receptor RNA or by detecting GnRH receptor protein, by using a label causing or inducing a signal that is a radioactive label or a fluorescence label, wherein said label may be directly conjugated to the GnRH receptor ligand or to antibodies directed against the GnRH receptor ligand.

5. The method of claim 1, wherein the tumor cells are derived from tumors selected from the group consisting of malignant and non-malignant brain cells and/or nervous system cells and/or meninges and/or Kaposi cells and/or oat cell and/or reactive cells, wherein the reactive cells further comprise reactive astrocytes and reactive neuroglia cells.

6. The method of claim 1, wherein the compound of step (b) is selectively administered combined with an additional GnRH analogue that is selected from Table 1.

7. The method according to claim 1, wherein the tumor cells are erythropoietin-receptor positive.

8. The method according to claim 7, wherein the compound of step (b) is selectively administered combined with a replication-decreasing amount of an erythropoietin analogue, wherein the erythropoietin analogue is human erythropoietin.

9. The method of claim 7, wherein the compound of step (b)is selectively administered combined with a replication-decreasing amount of a thrombopoietin agonist, wherein said thrombopoietin agonist interacts with the EPO receptor to thereby cause a decrease in tumor cell replication and/or an increase in tumor cell apoptosis.

10. The method of claim 9, wherein the thrombopoietin agonist is Eltrombopag.

11. The method according to claim 1, wherein the compound of step (b) is selectively administered combined with a replication-decreasing amount of a human gonadotropin inhibiting hormone peptide selected from an RFamide-related peptide-1 an RFamide-related peptide-3 or a biologically functionally derivative thereof.

12. The method of claim 1, wherein the compound of step (b) is selectively administered combined with a replication-decreasing amount of an anti-angiogenic substance, wherein the anti-angiogenic substance is zibotentan or a pharmaceutically acceptable salt thereof.

13. The method according to claim 1 wherein the compound of step (b) is used in combination with a cytotoxic substance.

14. The method according to claim 13, wherein the cytotoxic substance is coupled with the compound or a pharmaceutically acceptable salt thereof.

15. The method according to claim 14, wherein the cytotoxic substance is coupled with D-Lys6-GnRH, D-Lys-6-GnRH II, Lamprey GnRH II, Lamprey GnRH III, or a pharmaceutically acceptable salt thereof.

16. The method according to claim 13, wherein the cytotoxic substance is a fluorescent substance.

17. The method of claim 1, wherein the compound of step (b) is selectively administered by subcutaneous, intracutaneous, intramuscular, intravenous, intracranial, cerebral, intracerebral, intraspinal, subdural, extracerebral, meningeal, pulmonary, intrapulmonary, tumoral, intratumoral, peritumoral or tumor region localized injection, gel implantation, by a sustained release implantation, by nasal, transnasal or intranasal application, by ocular or intraoculary application, by means of eye drops or, or by means of injection, by a subcutaneous ventricular cytostatic reservoir being connected to a cerebral ventricle, or by a carrier particle, wherein the particle is a microparticle, or by a nanoparticle, wherein the nanoparticle is a lipid nanoparticle or a magnetic nanoparticle.

18. A method of selectively treating a tumor in a subject using a plurality of compounds in succession to thereby reduce tumor cell replication comprising:
  (a) selecting the subject on the basis of the patient having a positive detection and/or determination of GnRH receptors and/or GnRH receptor concentration in a sample of tumor cells derived from the tumor;
  (b) selectively administering to the subject a first replication-decreasing amount of a first compound comprising IN3 or a pharmacologically acceptable salt thereof;
  (c) selectively administering subsequent to step (b) a first treatment with a second compound comprising an GnRH agonist selected from the group consisting of leuprorelin, triptorelin, buserelin, goserelin, nafarelin, or a pharmacologically acceptable salt of any thereof, wherein the tumor is selected from the group consisting of lung oat-cell carcinoma, neurally-derived oat-cell carcinoma, Kaposi sarcoma, malignant glioma, and melanoma; and
  (d) quantifying tumor recidivation and GnRH receptor determination to detect tumor growth activity or tumor recurrence,
    wherein if tumor growth activity or tumor recurrence is not detected, treatment is discontinued, and
    wherein if tumor growth activity or tumor recurrence is detected, a second treatment with a GnRH agonist is selectively administered.

19. The method of claim 18, wherein if tumor growth activity or tumor recurrence is detected, the method further comprises selectively administering a second replication-decreasing amount of IN3 or a pharmacologically acceptable salt thereof followed by a second treatment with the second compound comprising the GnRH agonist or a pharmacologically acceptable salt thereof.

* * * * *

```
                      SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence, primer for polymerase chain
      reaction

<400> SEQUENCE: 1
gcttgaagct ctgtcctggg a                                              21

<210> SEQ ID NO 2
<211> LENGTH: 17
<212> TYPE: DNA
<213> ORGANISM: Artificial Sequence
<220> FEATURE:
<223> OTHER INFORMATION: Synthetic sequence, primer for polymerase chain
      reaction

<400> SEQUENCE: 2
cctaggacat agtaggg                                                   17
```